US009907740B2

(12) United States Patent
Hagel et al.

(10) Patent No.: US 9,907,740 B2
(45) Date of Patent: Mar. 6, 2018

(54) INCREASING MUSCULAR VOLUME IN A HUMAN USING HYALURONIC ACID

(71) Applicants: Jeffrey Hagel, Surrey (CA); Damian Naqvi, Laval (CA)

(72) Inventors: Jeffrey Hagel, Surrey (CA); Damian Naqvi, Laval (CA)

(*) Notice: Subject to any disclaimer, the term of this patent is extended or adjusted under 35 U.S.C. 154(b) by 208 days.

(21) Appl. No.: 14/761,793

(22) PCT Filed: Apr. 19, 2013

(86) PCT No.: PCT/CA2013/050307
§ 371 (c)(1),
(2) Date: Jul. 17, 2015

(87) PCT Pub. No.: WO2014/110656
PCT Pub. Date: Jul. 24, 2014

(65) Prior Publication Data
US 2015/0359721 A1    Dec. 17, 2015

Related U.S. Application Data

(60) Provisional application No. 61/753,814, filed on Jan. 17, 2013.

(51) Int. Cl.
| | | |
|---|---|---|
| *A61K 31/728* | (2006.01) | |
| *A61K 31/738* | (2006.01) | |
| *A61K 8/73* | (2006.01) | |
| *A61Q 19/00* | (2006.01) | |
| *A61K 9/00* | (2006.01) | |

(52) U.S. Cl.
CPC ............ *A61K 8/735* (2013.01); *A61K 9/0019* (2013.01); *A61K 31/728* (2013.01); *A61K 31/738* (2013.01); *A61Q 19/00* (2013.01); *A61K 2800/74* (2013.01); *A61K 2800/91* (2013.01)

(58) Field of Classification Search
CPC ... A61K 9/19; A61K 9/24; A61K 9/41; A61K 31/728; A61K 31/738; A61L 27/20
See application file for complete search history.

(56) References Cited

U.S. PATENT DOCUMENTS

2005/0226936 A1* 10/2005 Agerup ................. A61L 15/20
424/489
2011/0077737 A1   3/2011 Stroumpoulis et al.

FOREIGN PATENT DOCUMENTS

| WO | 2005032562 A1 | 4/2005 |
| WO | 2005097218 A2 | 10/2005 |
| WO | 2008094697 A2 | 8/2008 |
| WO | 2010015901 A1 | 2/2010 |

OTHER PUBLICATIONS

Newman, J. "Review of soft tissue augmentation . . . " Clin. Cosmet. Invest. Dermatol. (2009) vol. 2, pp. 141-150.*

Bhat et al., "Breast Augmentation with Implants Following Previous Enhancement with Macrolane Filler Injections", Aesthetic Plastic Surgery, 2011, pp. 670-671, vol. 35.
Goisis et al., "Breast Augmentation after Macrolane Filler Injections", Aesthetic Plast Surgery, 2011, pp. 684-686, vol. 35 No. 4.
Gold et al., "Soft Tissue Augmentation in Dermatology—2009 Update", Journal of Cutaneous and Aesthetic Surgery, 2010, pp. 2-10, vol. 3.
Hertegard et al., "Viscoelastic Properties of Rabbit Vocal Folds After Augmentation", Otolaryngology Head and Neck Surgery, 2003, pp. 401-406, vol. 128, No. 3.
Kwak et al., "The Effects of Penile Girth Enhancement Using Injectable Hyaluronic Acid Gel, a Filler", Journal of Sexual Medicine, 2011, pp. 3407-3413, vol. 8.
Tous et al., "Influence of Injectable hyaluronic Acid Hydrogel Degradation Behavior on Infarction Induced Ventricular Remodeling", Biomacromolecules, 2011, pp. 4127-4135, vol. 12 No. 11.
Yoshimura et al., "Cell-Assisted Lipotransfer for Cosmetic Breast Augmentation: Supportive Use of Adipose-Derived Stem-Stromal Cells", Aesthetic Plastic Surgery, 2008, pp. 48-55, vol. 32.
International Search Report and Written Opinion for PCT/CA2013/050307 dated Oct. 17, 2013.
International Preliminary Report on Patentability (Chapter II) for PCT/CA2013/050307 dated May 19, 2015.
Third Party Observations for PCT/CA2013/050307 dated Mar. 6, 2015.
Supplementary European Search Report issued in European Application No. EP 13871347, dated Jul. 8, 2016, 8 pages.
Newman, "Review of Soft Tissue Augmentation in the Face," Clinical, Cosmetic and Investigational Dermatology, vol. 2, pp. 141-150 (2009).
"Technical Aspects of Treatment with Macrolane for Breast Enhancement", Q-Med AB, 4 pages.
McCleave et al., "Breast Enhancement Using Macrolane™: A Report of Complications in Three Patients and a Review of this New Product", Journal of Plastic, Reconstructive & Aesthetic Surgery, 2010, pp. 2108-2111, vol. 63.
Siebert et al., "The Latest Information on Macrolane™: Its Indications and Restrictions", Annales de Chirurgie Plastique Esthetique, Apr. 2014, pp. e1-e11, vol. 59, No. 2.

\* cited by examiner

*Primary Examiner* — Leigh C Maier
(74) *Attorney, Agent, or Firm* — Thompson Coburn LLP

(57) ABSTRACT

A method for increasing muscular volume of a muscle in a human is provided. The method comprises injecting a composition comprising hyaluronic acid (HA) into one or more than one location of a muscle, thereby increasing the muscular volume as compared to before the injection. The muscle may be an arm, leg, chest, back or buttock muscle, or any other desired muscle. A method for altering a contour of a muscle in a human is also provided, which comprises obtaining an image of the contour of the muscle, determining a new contour, injecting an HA composition into one or more than one location of the muscle to obtain the new contour, thereby altering the contour as compared to before the injection. A use of a composition comprising HA for increasing muscular volume of a muscle in a human is also provided, where the composition is for injection into muscle.

14 Claims, 11 Drawing Sheets

INCREASING MUSCULAR VOLUME IN A HUMAN USING HYALURONIC ACID

CROSS-REFERENCE TO RELATED APPLICATIONS

This application is the U.S. National Stage of International Application PCT/CA2013/050307, filed on Apr. 19, 2013, which claims benefit of U.S. Provisional Patent Application Ser. No. 61/753,814, filed on Jan. 17, 2013, the entire contents of both are hereby incorporated by reference for all purposes.

FIELD OF INVENTION

This invention relates to increasing muscular volume of a muscle in a human.

BACKGROUND OF THE INVENTION

Body image and health is of interest for many humans. For some, there is a need to have shapely arms, legs, pectoral and gluteal muscles and the like, often together with improved strength and overall fitness. Given the more hectic lifestyles of people in last few years, there has been an increased interest in finding simple, non-invasive and safe methods for improving the appearance and strength of a person's arms, legs, pectoral, gluteal and other muscles, without having to expend too much time and effort.

Hyaluronic acid (HA), also known as hyaluronan or hyaluronate, is a well-known, naturally occurring polysaccharide that is secreted by fibroblasts and found in all mammals. It is a long unbranched, high molecular weight polysaccharide composed of repeating dimeric units of D-glucuronic acid and N-acetylglucosamine, and is found in all tissues in the body, with higher amounts in the skin, the vitreous humor of the eye and connective tissues. When not bound to other molecules, HA binds to water and forms a highly viscous solution, giving it a jelly-like substance.

HA currently has a variety of uses, including cosmetic and therapeutic uses. With respect to therapeutic uses, HA has been used as a replacement for the liquid vitreous of the human eye to aid in ophthalmic surgery; to treat osteoarthritis, by intra-articular injection directly into the synovial fluid in the knee (for example, George (1998) *Ann. Rheum. Dis.* 57: 637-40; Weiss et al. (1981) *Arthritis Rheum.* 11 (suppl 1): 143-4); to manage and treat chronic tennis elbow or lateral epicondylosis (for example, Petrella et al. (2010) *Sports Medicine, Arthroscopy, Rehabilitation, Therapy & Technology* 2:4; Orchard and Kountouris (2011) *BMJ* (2011) 342: d2687); and to treat vocal fold paralysis by injection into the thyroarytenoid (TA) muscle of the larynx (for example, Wang et al. (2011) *Journal of Voice* 26(4): 506-514; Lee et al. (2010) *Thyroid* 20(5): 513-517). Cosmetically, HA has been used to provide facial enhancements and improve the skin's contour and reduce depressions in the skin due to acne, scars, injury or lines by subcutaneous injection, directly under a person's skin (for example, Duranti et al. (1998) *Dermatol. Surg.* 24: 1317-25; Jordan (2003) *Can. J. Ophthalmol.* 38: 285-8; Cheng et al. (2002) *Otolaryngol. Clin. North Am.* 35:73-85). In addition to being used as the primary agent, HA has been used as a secondary agent, such as a viscosity-inducing component (for example, Aydin et al. (2007) *Auris Nasus Larynx* 34(3): 333-8; US 2008/0044476), or as a biocompatible polymer (for example, KR 2008/0100126).

Recently, Macrolane™ (Q-med AB), a gel derived from HA, has been used for body contouring and breast augmentation in Europe. It has been used for reshaping and boosting volume in specific areas of the body, such as the buttocks, calves, chest muscles and arms, and filling concavities and scars on the body (see URL: stureplanskliniken.com/macrolane.asp; and familyhealthguide.co.uk/cosmetic-surgery/macrolane.html). Macrolane™ is intended solely for injection into the subcutaneous skin layer above the muscle, but not for intramuscular or intravascular injection (Q-Med AB Macrolane Clinical Guide; or see URL: myfacemybody.com/procedures/non-surgical/injectable-body-contouring-macrolane/).

SUMMARY OF THE INVENTION

This invention relates to increasing muscular volume of a muscle in a human. The present disclosure further describes injection of hyaluronic acid into muscle of a human for increasing the muscular volume of the muscle.

The present disclosure provides a method for increasing muscular volume of a muscle in a human by injecting a composition comprising hyaluronic acid (HA) into a muscle of interest at one or more than one location in the muscle, for example, two or more, three or more, or four or more locations in the muscle, thereby increasing the muscular volume as compared to the muscular volume before the composition is injected into the muscle. The injection into the muscle may be done for cosmetic purposes or to improve muscle function or performance. The muscle injected may be selected from the group of an arm muscle, a leg muscle, a chest muscle, a back muscle and a buttock muscle.

The composition comprising HA may be any composition comprising HA. The HA of the composition may be of a molecular weight in the range of approximately 5,000 Daltons to approximately 10 million Daltons, or any amount therebetween, for example about 5,000 Daltons to about 6 million Daltons, about 5,000 Daltons to about 2 million Daltons, about 5,000 Daltons to about 1 million Daltons, or for example from about 5,000 Daltons to about 500,000 Daltons.

The concentration of cross-linked HA in the composition may range from approximately 0.5 mg/mL to approximately 40 mg/mL, or any amount therebetween, for example, from approximately 0.5 mg/mL to approximately 35 mg/mL or any amount therebetween, from approximately 0.5 mg/mL to approximately 30 mg/mL or any amount therebetween, from approximately 0.5 mg/mL to approximately 25 mg/mL or any amount therebetween, or from approximately 0.5 mg/mL to approximately 20 mg/mL or any amount therebetween (see, for example, US 20100316683, which is incorporated by reference herein).

The viscosity and the elasticity (or stiffness) of the composition may be any viscosity and elasticity that is suitable for injection. For example, the elastic modulus (G') of the HA composition may range from about 15 Pa to about 900 Pa, which range is not to be considered limiting (see, for example, Kablik J. et al., *Dermatol Surg* 2009; 35: 302-312, which is incorporated by reference herein).

The composition comprising HA may be any commercially available HA product. For example, the HA composition may be selected from any one of the following commercially available HA products: Juvéderm® Ultra, Juvéderm® UltraPlus, Juvéderm® Plus, Captique®, Hylaform®, RESTYLANE®, RESTYLANE® Perlane®, RESTYLANE® SubQ, RESTYLANE® Touch, Prevelle®, Prevelle Silk®, Macrolane™, Hyalgan®, Synvisc® (also known as Hylan G-F 20), Supartz® (also known as Artz® or Artzal), Modélis Shape or Orthovisc®.

Any number of muscles of a human may be directly injected with the composition, such as, for example, the biceps muscle; the triceps muscle; the brachioradialus muscle; the brachialis muscle (brachialis anticus); the superficial compartment wrist flexors; the deltoid muscle; the biceps femoris, the gracilis, the semitendinosus and the semimembranosus muscles of the hamstrings; the rectus femoris, vastus lateralis, vastus medialis and vastus intermedius muscles of the quadriceps; the gastrocnemius (lateral and medial), tibialis anterior, and the soleus muscles of the calves; the pectoralis major and the pectoralis minor muscles of the chest; the latissimus dorsi muscle of the upper back; the rhomboids (major and minor); the trapezius muscles that span the neck, shoulders and back; the rectus abdominis muscles of the abdomen; and the gluteus maximus, gluteus medius and gluteus minimus muscles of the buttocks.

Also provided is the injection of the composition intramuscularly into the muscle. The present disclosure provides for a volume of injected HA composition ranging from approximately 0.01% to approximately 25% of the total muscle volume of the muscle to be injected, or any amount therebetween. Depending upon the volume of the muscle to be treated, the HA composition may be injected at one to 100 locations within the muscle at a plurality of injection sites. The injections may be either uniformly distributed along the muscle to be treated or concentrated at one or more injection sites along the muscle to be treated, for example, two or more, three or more, or four or more injection sites, depending on the cosmetic effect and/or the muscle performance desired.

The composition may also be injected using a volumetric approach to provide the injection of the composition at a plurality of locations along a depth of a single injection site. This volumetric approach may involve injecting the composition while simultaneously withdrawing the needle or cannula from the distal-most aspect of a single injection site to the proximal-most aspect of the injection site, thereby distributing the composition in multiple layers of the muscle at the single injection site. This process of injecting the composition at one or more than one location of a single injection site may comprise the following: (a) piercing the proximal muscular sheath at the injection site with the instrument for injection; (b) positioning the instrument at the distal-most aspect of the muscular sheath at the injection site (i.e., a first location); (c) at the first location, pulling back on the instrument to create negative pressure and prevent intravascular injection and then injecting the composition; (d) slightly withdrawing the instrument toward the proximal aspect of the muscular sheath to a second location; (e) at the second location, pulling back on the instrument to create negative pressure and then injecting the composition at the second location; and (f) repeating steps (d) and (e) at any number of additional locations, depending on the desired effect, with each additional location being positioned closer to the proximal-most aspect of the muscular sheath as compared to the immediately preceding location.

The present disclosure also provides for the real-time guidance of the injection of the composition into the muscle to be injected. In this regard, the composition is injected with the assistance of an ultrasound machine in real-time, or any other method for imaging muscle that is known in the art, to visualize the muscle of interest while injecting the composition.

Further described herein is the intramuscular injection of approximately 0.01 cc/kg of body weight of an HA composition to approximately 6.0 cc/kg of body weight of an HA composition into a single muscle to be injected, or any amount therebetween. For example, approximately 0.01 cc/kg of body weight to approximately 2.0 cc/kg of body weight in total may be injected per biceps or triceps muscle, or any amount therebetween; approximately 0.01 cc/kg of body weight to approximately 1.5 cc/kg of body weight in total may be injected per brachialis muscle of the arm, or any amount therebetween; approximately 0.01 cc/kg of body weight to approximately 0.8 cc/kg of body weight in total may be injected per brachioradialis muscle of the arm, or any amount therebetween; approximately 0.01 cc/kg of body weight to approximately 0.8 cc/kg of body weight in total may be injected per superficial compartment wrist flexor muscle, or any amount therebetween; approximately 0.01 cc/kg of body weight to approximately 1.3 cc/kg of body weight in total may be injected per lateral gastrocnemius muscle of the calf, or any amount therebetween; approximately 0.01 cc/kg of body weight to approximately 1.3 cc/kg of body weight in total may be injected per medial gastrocnemius muscle of the calf, or any amount therebetween; approximately 0.01 cc/kg of body weight to approximately 3.2 cc/kg of body weight in total may be injected per soleus muscle of the calf, or any amount therebetween; approximately 0.01 cc/kg of body weight to approximately 5.0 cc/kg of body weight in total may be injected per total quadricep muscle, or any amount therebetween; approximately 0.01 cc/kg of body weight to approximately 5.6 cc/kg of body weight in total may be injected per total hamstring muscle, or any amount therebetween; approximately 0.01 cc/kg of body weight to approximately 6.0 cc/kg of body weight in total may be injected per gluteus maximus muscle of the buttocks, or any amount therebetween; approximately 0.01 cc/kg of body weight to approximately 2.3 cc/kg of body weight in total may be injected per gluteus medius muscle of the buttocks, or any amount therebetween; approximately 0.01 cc/kg of body weight to approximately 2.3 cc/kg of body weight in total may be injected per deltoid muscle, or any amount therebetween; approximately 0.01 cc/kg of body weight to approximately 2.3 cc/kg of body weight in total may be injected per trapezius muscle, or any amount therebetween; approximately 0.01 cc/kg of body weight to approximately 3.8 cc/kg of body weight in total may be injected per pectoralis major muscle of the chest, or any amount therebetween; approximately 0.01 cc/kg of body weight to approximately 4.4 cc/kg of body weight in total may be injected per latissmus dorsi muscle of the back, or any amount therebetween; or approximately 0.01 cc/kg of body weight to approximately 0.5 cc/kg of body weight in total may be injected per rectus abdominis muscle of the abdomen, or any amount therebetween.

The injections may also be repeated on a periodic basis from a repeat treatment per month, every two months, every 3 months, every 4 months, every 6 months, every 12 months, every 15 months, every 18 months, every 21 months, every 24 months, every 26 months, every 28 months or every 30 months, as desired. Repeat treatments may be performed to either maintain the muscular volume or progressively augment the muscular volume over time.

For those repeat injections done to maintain muscular volume (i.e., no further augmentation of the muscle), the additional injections of the HA composition may be repeated every 1, 2, 3, 6, 12, 18, 24 or 30 months, or any time therebetween. These maintenance injections may comprise low volume doses, for example, without limitation, doses of approximately 0.1 cc/kg to approximately 1.0 cc/kg of body weight of the HA composition, or any amount therebetween, are injected into the muscle of interest. The dose injected and the frequency of the repeat injections may depend on the physical activity of the individual patient.

For those repeat injections done to progressively augment the muscle over time (i.e., to achieve a greater muscular volume over time), the additional injections of the HA composition may be done in a step-wise manner. An initial volume ranging from approximately 0.1 cc/kg to approximately 6.0 cc/kg of body weight may be injected into the muscle of interest, followed by additional injections of approximately 0.1 cc/kg to approximately 6.0 cc/kg of body weight of the HA composition injected into the same muscle at approximately 1 month to approximately 8 months or later after the initial injection, or any time therebetween, to achieve additive effects on the initial injection.

The present disclosure also provides for a method of altering a contour of a muscle of a human that comprises the steps of obtaining an image of the contour of the muscle, determining a new contour of the muscle, injecting a composition comprising HA into one or more than one location of the muscle, for example, two or more, three or more, or four or more locations, to obtain the new contour of the muscle, which injection results in an alteration of the contour of the muscle.

The present disclosure also provides for a use of the composition comprising HA, as defined above, for increasing muscular volume of a muscle in a human compared to the muscular volume of the muscle in the absence of said composition, wherein the composition is for injection into the muscle.

The present disclosure further provides for a kit comprising the composition comprising HA, as defined above, and instructions for intramuscular injection of the composition into a muscle in a human.

This summary of the invention does not necessarily describe all features of the invention. Other aspects, features and advantages of the present disclosure will become apparent to those of ordinary skill in the art upon review of the following description of specific embodiments of the invention.

BRIEF DESCRIPTION OF THE DRAWINGS

These and other features of the invention will become apparent from the following description in which reference is made to the appended drawings, wherein.

DETAILED DESCRIPTION

Figure 1A:
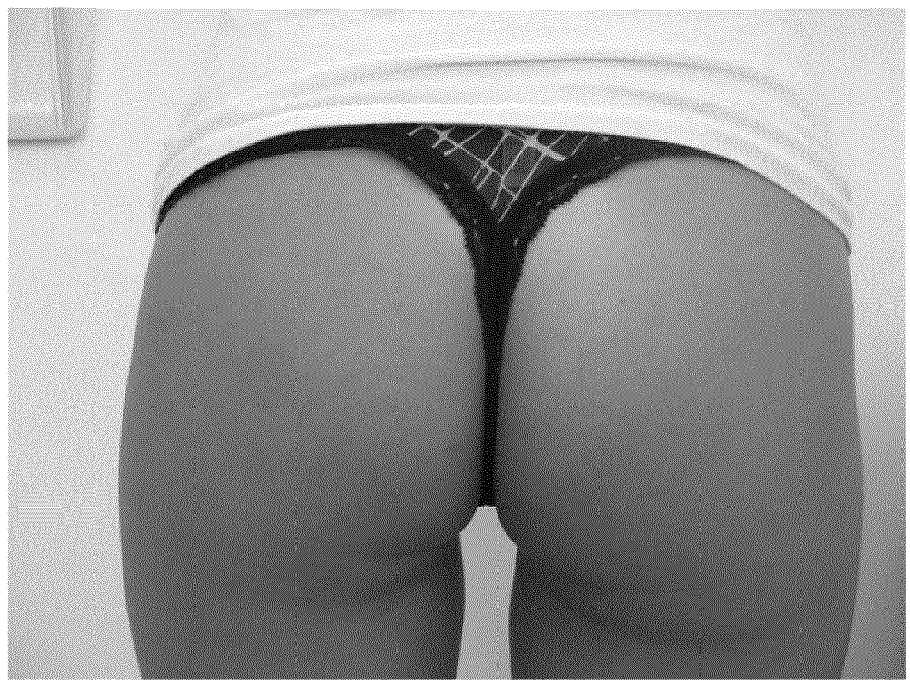
FIG. 1 presents a digital image of a posterior view of patient A's buttocks of Example 1 to illustrate the gluteus maximus muscle: (A) prior to injection of the composition comprising HA; and (B) at 8 weeks post-injection of the composition comprising HA.

The present disclosure relates to increasing muscular volume in a muscle of a human. This invention also relates to the injection of hyaluronic acid into a muscle of a human for increasing the muscular volume of the muscle.

The present disclosure provides a method for increasing the muscular volume of a muscle in a human by injecting a composition comprising hyaluronic acid (HA) into the muscle. The composition is injected into the muscle of interest at one or more than one location in the muscle, for example, two or more, three or more, or four or more locations, which results in an increase in the muscular volume as compared to before the composition is injected into the muscle.

The composition for intramuscular injection into a muscle of a human comprises hyaluronic acid as the primary agent. The terms "hyaluronic acid" and "HA" are used interchangeably herein and have the same meaning.

As used herein, "hyaluronic acid" or "HA" means the compound constituted of the series of repeating dimeric units of D-glucuronic acid and N-acetylglucosamine. The term "hyaluronic acid" is also intended to include not only elemental hyaluronic acid, but hyaluronic acid with traces of other elements or in various compositions with other elements, as long as the chemical and physical properties of hyaluronic acid remain unchanged. In addition, the term "hyaluronic acid" as used in the present disclosure includes natural formulas, synthetic formulas or a combination of these natural and synthetic formulas.

The HA used in the present disclosure may be extracted from animal tissue such as rooster combs or umbilical cords or from bacterial cultures such as those of hemolytic group A or C Streptococci. Those skilled in the art will appreciate that the HA of the present disclosure may be obtained from any other source so long as it is pure enough to avoid provoking an adverse or toxic reaction in the human in which it is introduced.

The HA used in the present disclosure may be non-stabilized and non-chemically modified in the form, in particular, of esters or amides, or the HA may be chemically modified and/or cross-linked derivatives (i.e., exhibiting intra- and/or interchain bridges). Cross-linking refers to a process in which the individual polymer chains of HA are chemically bound (or "cross-linked) together, transforming a liquid HA into a soft solid or gel. Cross-linking substantially reduces the miscibility of the HA with water, but does not change the physicochemical characteristics and the biological properties of the HA. Any technique known in the art may be used for cross-linking the HA, including the use of cross-linking agents known in the art, such as divinyl sulphone (DVS), 2,7,8-diepoxyoctane (DEO), and 1,4-butanediol diglycidyl (BDDE). Cross-linked HA compositions are known in the art, for example, Juvéderm® Ultra Plus, Juvéderm® Ultra, Prevelle®, Captique®, Hylaform® and RESTYLANE® (see, for example, Allemann, I. B. and Baumann, L. "Hyaluronic acid gel (Juvéderm™) preparations in the treatment of facial wrinkles and folds." *Clinical Interventions in Aging* 3(4): 629-634, 2008, herein incorporated by reference).

As used herein, "cross-linked HA" means HA that has been modified using cross-linking agents, as described above, such that the individual HA polymer chains are cross-linked to other HA polymer chains.

The compositions of the present disclosure may comprise from about 0.5 mg/mL cross-linked HA to about 40 mg/mL cross-linked HA (gel concentration), with the remainder of the composition comprising any aqueous, biocompatible solution known in the art, such as water, phosphate containing buffers, and sodium chloride containing buffers. The composition may further comprise non-cross-linked HA. The concentration of cross-linked HA in the compositions of the present disclosure may be adjusted by one skilled in the art according to the molecular weight of the HA, the effect desired, for example, cosmetic or muscle enhancement, and the particular muscle to be injected. By way of example, the concentration of cross-linked HA in the composition can vary from approximately 0.5 mg/mL to approximately 40 mg/mL, or any amount therebetween, from approximately 0.5 mg/mL to approximately 35 mg/mL, from approximately 0.5 mg/mL to approximately 30 mg/mL, from approximately 0.5 mg/mL to approximately 25 mg/mL, from approximately 0.5 mg/mL to approximately 20 mg/mL, or from approximately 0.5, 1, 1.5, 2.0, 2.5, 3.0, 3.5, 4.0, 4.5, 5.0, 6.0, 7.0, 8.0, 9.0, 10.0, 12.0, 15.0, 18.0, 20.0, 22.0, 24.0, 25.0, 26.0, 28.0, 30, 35, 40 mg/mL, or any amount therebetween (see, for example, US 20100316683, which is incorporated by reference herein).

With respect to the individual polymer chains of HA in a composition, the percentage of cross-linking within an individual HA polymer chain (i.e. the degree of cross-linking for an individual HA polymer chain) in the composition may be between approximately 0% and approximately 20% of the HA polymer chain, or any amount therebetween.

Commercially available HA compositions may also be used. Examples of commercially available HA products that may be used include, but is not limited to, Juvéderm® (a highly cross-linked hyaluronic acid product sold by Allergan, Inc.) including Juvéderm® Plus, Juvéderm® Ultra Plus, Juvéderm® Ultra; Prevelle®; Captique® (non-animal stabilized HA); Hylaform® (highly purified form of HA); RESTYLANE® (non-animal stabilized HA products sold by Q-Med AB), including RESTYLANE® Perlane®, RESTYLANE® Touch, and RESTYLANE® SubQ; Macrolane™ (a more viscous RESTYLANE® product sold by Q-Med AB); Hyalgan® (a viscous solution of the sodium salt of HA naturally derived from rooster combs without chemical modification); Synvisc® or Hylan G-F 20 (a viscous mixture of chemically cross-linked HA, composed of approximately 80% hylan A and approximately 20% of hylan B); Supartz® (a highly purified sodium hyaluronate extracted from rooster combs and marketed as Artz® or Artzal outside of the US); Modélis Shape; and Orthovisc® (a viscous solution derived from rooster combs). However, one of skill in the art will appreciate that any acceptable HA product or any composition comprising HA and/or its derivatives suitable for introduction into a human can be used in accordance with the present disclosure.

In addition to HA, derivatives of HA or a combination thereof, the compositions of the present disclosure may further comprise any one or more of the following: an aqueous carrier component, a buffer component, a tonicity component, a biocompatible preservative component or a resuspension component. The physicochemical characteristics of the HA of the composition of the present disclosure may be varied depending on the particular muscle injected and the effect desired, for example, a cosmetic (volume-based effect), or a muscle enhancement (performance-based effect).

The molecular weight of the HA present in the composition may vary to a large extent depending on the muscle to be injected and desired effect. The molecular weight can be in the range of about 5,000 Daltons to about 10 million Daltons, or any amount therebetween, for example, from approximately 5,000 Daltons to approximately 6 million Daltons or any amount therebetween, from approximately 5,000 Daltons to approximately 2 million Daltons or any amount therebetween, from approximately 5,000 Daltons to approximately 1 million Daltons, or any amount therebetween, or from approximately 5,000 Daltons to approximately 500,000 Daltons, or any amount therebetween.

The diameters of the gel particles of the HA composition may be in the range of, but not limited to, approximately 50 µm to approximately 2000 µm, or any amount therebetween, for example, from approximately 50 µm to approximately 1500 µm or any amount therebetween, from approximately 50 µm to approximately 1000 µm or any amount therebetween, from approximately 50 µm to approximately 800 µm or any amount therebetween, or from approximately 50 µm to approximately 400 µm or any amount therebetween. As a result, the gel particle size of the HA composition may be in the range of approximately 800 gel particles per mL to approximately 1,000,000 gel particles per mL, or any amount therebetween, depending on the desired cosmetic or muscle performance effect. For example, the gel particle size of the HA composition may be from approximately 1,000 gel particles per mL to approximately 500,000 gel particles per mL, from approximately 1,000 gel particles per mL to approximately 250,000 gel particles per mL, from approximately 1,000 gel particles per mL to approximately 100,000 gel particles per mL, from approximately 1,000 gel particles per mL to approximately 50,000 gel particles per mL, from approximately 1,000 gel particles per mL to approximately 10,000 gel particles per mL, or any amount therebetween. Alternatively, homogenous gel HA compositions, which do not use sizing technology, may be used for injection, such as, but not limited to, Juvéderm™'s hylacross technology.

Viscosity and elasticity of the composition comprising HA and/or its derivatives will be any viscosity and elasticity that is suitable for injection. For example, the elastic modulus (G') of the HA composition may range from about 15 Pa to about 900 Pa, which range is not to be considered limiting (see, for example, Kablik et al., Dermatol Surg 2009; 35: 302-312, which is incorporated by reference herein).

Examples of certain commercially available HA compositions and the properties of those compositions are shown in the table below. These examples are exemplary only and should not be considered limiting in any manner:

|  | Hylaform | Hylaform Plus | Prevelle | Restylane | Perlane | Juvederm 30HV |
| --- | --- | --- | --- | --- | --- | --- |
| Total HA concentration (mg/mL) | 5.5 | 5.5 | 5.5 | 20 | 20 | 24 |
| Gel-to-fluid ratio | 98:2 | 98:2 | 98:2 | 75:25 | 75:25 | 60:40 |
| HA gel concentration (mg/mL) | 5.4 | 5.4 | 5.4 | 15.0 | 15.0 | 14.4 |
| Degree of HA modification (%) | 23 | 23 | 23 | 3 | 3 | 10 |
| Percentage of cross-linked HA | 12 | 12 | 12 | 1.2 | 1.4 | 2 |
| Dilution durability/ percentage swelling | <25 | <25 | <25 | 50 | 50 | 300 |
| G' modulus (Pa) | 140-220 | 140-220 | 230-260 | 660 | 588 | 105 |
| Average particle size (μm) | 500 | 700 | 350 | 300 | 650 | 300 |

Source: Kablik et al. "Comparative Physical Properties of Hyaluronic Acid Dermal Fillers." Dermatol Surg 2009; 35: 302-312.

The compositions according to the present disclosure are formulated for injection into the muscle of a human. As used herein, the term "muscle" refers to a muscle in the arm, leg, chest, back, abdomen, buttocks and any other area of the human body that a person desires to be more shapely and/or more muscular.

A person skilled in the art would understand that prior to injection of the compositions into the muscles of a human, patient health is assessed to ensure that a relative standard of patient health is met prior to starting the treatments, as described herein. The expression "relative standard of patient health" means that, at a minimum, the patient has no significant relevant pre-existing medical conditions and is generally considered to be in a satisfactory state of physical, mental and social well-being by a medical professional prior to starting the treatments described herein.

The present disclosure contemplates injection of a composition described herein into the muscles of an arm, if a human desires more shapely arms, more muscular arms, or a combination thereof, when compared to the shape or performance of the arm prior to HA administration. The composition can be injected into any muscle in the arm at one or more than one location, for example two or more, three or more, or four or more locations. The location of the injection sites, or volume injected will depend on the desired shape, muscle performance or a combination thereof desired. For example, an HA composition can be injected directly into one or more of the biceps muscle (biceps brachii), the brachialis muscle, the brachioradialus muscle, the triceps muscle (triceps brachii), the superficial compartment wrist flexors, or other muscle in the arm to give the desired shape to the arm. In addition, an HA composition described herein may be injected into the deltoid muscle, if a person wishes to re-shape or provide muscular definition to the contour of the shoulder.

The present disclosure also contemplates injection of an HA composition described herein into the muscles of a leg, if a human desires more shapely legs, more muscular legs, or a combination thereof, when compared to the shape or performance of the leg prior to HA administration. The composition can be injected into any muscle in the leg at one or more than one location, for example two or more, three or more, or four or more locations, and will depend on the desired shape, muscle performance, or a combination thereof that is desired. For example, the composition can be injected directly into one or more of the hamstrings, including the biceps femoris, the gracilis, the semitendinosus and semimembranosus muscles of the hamstrings; the quadriceps, including the rectus femoris, vastus lateralis, vastus medialis and vastus intermedius muscles of the quadriceps; the calves, including the gastrocnemius (lateral and medial), tibialis anterior, and the soleus muscles of the calves; or any other muscle in the legs to give the desired shape or muscle performance to the legs.

In a similar manner to that described above, the present disclosure further contemplates injection of a composition described herein into the pectoral muscles of a person's chest at one or more than one location, for example two or more, three or more, or four or more locations. The composition can be injected directly into the pectoralis major and/or pectoralis minor muscles of the chest and/or any other muscle in the chest to give the desired effect. In addition, the composition may be injected into the muscles of the abdomen, including, without limitation, the rectus abdominis.

The present disclosure further contemplates injection of a composition described herein into the muscles of the buttocks, if the person desires more shapely buttocks, more muscular buttocks, or a combination thereof, when compared to the shape or performance of the leg prior to HA administration. The composition can be injected into any muscle in the buttocks at one or more than one location, for example two or more, three or more, or four or more locations, and will depend on the desired shape, muscle performance, or a combination. For example, the composition can be injected directly into the gluteus maximus, gluteus medius, gluteus minimus, or any other muscle in the buttocks to give the desired effect.

Additionally, a person may further wish to add muscular definition and contour to his/her back. The present disclosure contemplates injection of the composition comprising HA into any back muscle, as well as any other muscle of a person's body at one or more than one location, for example two or more, three or more, or four or more locations. For example, but without limitation, the composition can be injected directly into the latissimus dorsi of the upper back, the rhomboids (major and minor) and/or the trapezius muscles that span the neck, shoulders and back.

It is to be understood that a person may obtain injections into one or more muscle groups at a time, for example, two or more, three or more, or four or more muscle groups at a time, so that, for example, the arms, legs and buttocks may be treated during one visit with a medical practitioner.

As used herein, the term "muscular volume" refers to the total volume contained within the muscular sheath (otherwise known as the epimysium) of a muscle. This includes the non-contractile muscle cell fluid (sarcoplasm) of a muscle, which generally accounts for approximately 25-30% of a muscle size, and the contractile component of the muscle, including individual myocytes. "Muscular volume" can be measured by assessing the cross-sectional area of the muscle of the arm, leg, back, or buttock using standard techniques as would be known in the art, such as ultrasound or magnetic resonance imaging (MRI), by determining the profile of the muscle, for example by determining the height, width, or both, of an arm or leg, or the side profile of a chest, back or buttock, or by using any other clinical measurements known in the art.

The present disclosure contemplates an increase in muscular volume by intramuscular injection of a composition comprising HA into a muscle of interest. Injection into the muscle of a composition comprising HA increases the muscular volume of the muscle of interest; i.e., the cross-sectional area of that muscle. The increase in muscular volume can be determined by measuring the circumference of the muscle or the area of the body that the muscle is located before and after injection with the composition comprising HA.

The injections used in the methods of the present disclosure can be made at one or more than one location within the muscle of interest, for example, two or more, three or more, or four or more locations, and at one or more than one depth per injection site between the proximal aspect of the muscle sheath ("muscle sheath" is otherwise known as the epimysium) and the distal aspect of the muscle sheath, such as two or more, three or more, or four or more depths per injection site. For example, for muscles on top of and attached to a bone, the "proximal aspect" refers to the side of the muscle sheath that is closest to the surface of the skin and the "distal aspect" refers to the side of the muscle sheath furthest from the surface of the skin and closest to the bone. The intramuscular injections can be made, for example, without limitation, at a depth of approximately 0 cm to approximately 10 cm or any amount therebetween, from the proximal aspect of the muscle sheath. For example, from about 0, 0.1, 0.2, 0.5, 1.0, 1.25, 1.5, 2.0, 2.5, 3.0, 3.5, 4.0, 4.5, 5.0, 5.5, 6.0, 6.5, 7.0, 7.5, 8.0, 8.5, 9.0, 9.5, 10 cm, or any amount therebetween, from the proximal aspect of the muscle sheath. However, one of skill in the art will appreciate that the depth at which the injection is made may vary significantly between different individuals, the specific injection site, and the muscle into which the composition is introduced, the shape of the muscle that is desired, the desired cosmetic or muscle performance effect, or a combination thereof.

As used herein, the term "location" means the position inside the muscle where the composition is administered. The present disclosure contemplates injection at one or more than one location, for example, two or more, three or more, or four or more locations inside a muscle.

As used herein, the term "injection site" means the site at which the instrument for injecting the composition into a muscle is pierced through the muscular sheath for injection of the composition.

The present disclosure provides for the composition comprising HA and/or its derivatives being injected into one or more than one location of a muscle, for example two or more, three or more, or four or more locations of a muscle, which results in an increase in muscular volume, muscle performance, or both, in the muscle of interest. By way of example, the composition comprising HA may be injected at any one of one to about 100 locations, or any amount therebetween. For example, 1, 2, 3, 4, 5, 6, 7, 8, 9, 10, 15, 20, 25, 30, 35, 40, 45, 50, 55, 60, 65, 70, 75, 80, 85, 90, 92, 95, 98, 100 locations per muscle may be injected with the composition.

The locations of injection may be at a single injection site at one or more than one depth of the injection site, for example, two or more, three or more, or four or more depths of the injection site. The present disclosure contemplates the injection of the composition comprising HA and/or its derivatives thereof into one or more than one location, for example, two or more, three or more, or four or more locations, at a single injection site using a volumetric approach or any other method for distributing the composition into different layers of the muscle from the proximal aspect to the distal aspect of the muscle at a single injection site. For example, the instrument for injecting the composition into a muscle may be pierced through the proximal muscular sheath at an injection site and into the muscle up to the distal-most aspect of the muscular sheath and the composition injected at more than one location by injecting the composition while simultaneously withdrawing the instrument to the proximal-most aspect of the injection site. Multiple locations of a single injection site are, therefore, injected with hyaluronic acid as the needle is withdrawn towards the proximal-most aspect of the injection site. Negative pressure is applied prior to each injection to prevent intravascular injection. Thus, this process of injecting the composition at one or more than one location of a single injection site may comprise the following: (a) piercing the proximal muscular sheath at the injection site with the instrument for injection; (b) positioning the instrument at the distal-most aspect of the muscular sheath at the injection site (i.e., a first location); (c) pulling back on the instrument to create negative pressure at the first location and then injecting the composition at the first location; (d) slightly withdrawing the instrument toward the proximal aspect of the muscular sheath to a second location; (e) pulling back on the instrument to create negative pressure at the second location and then injecting the composition at the second location; and (f) repeating steps (d) and (e) at any number of additional locations, depending on the desired effect, with each additional location being positioned closer to the proximal-most aspect of the muscular sheath as compared to the immediately preceding location. The one or more than one location of a single injection site may further be equally spaced and/or mass proportionate aliquots of the composition may be injected at the one or more than locations. Therefore, the present disclosure provides for the injection of the composition at a plurality of locations, such as two or more, three or more, or four or more locations, at one or more than one depth along an injection site. The composition is therefore administered in multiple layers along the path of the injection instrument at an injection site.

The present disclosure also contemplates the locations of injection being at a plurality of injection sites, in addition to or in place of the locations of injection at a single injection site. The plurality of injection sites, for example, two or more, three or more, or four or more injection sites, may be spaced evenly along the muscle fibres of the muscle to be injected for uniform distribution of the composition. Alternatively, the injection sites may be concentrated at one or more than one position along the muscle. The position of the one or more than one injection sites and the distribution of the HA composition along the muscle will depend on the desired cosmetic and/or muscle performance effect of the muscle to be treated. For example, the injection sites may be spaced apart by about 1 mm to about 50 cm, or any amount therebetween, or spaced apart by about 1 mm to about 45 cm or any amount therebetween, for example, the injection sites may be spaced apart by about 1 mm, 2.5 mm, 5 mm, 0.75 mm, 1 cm, 1.5 cm, 2 cm, 3 cm, 4 cm, 5 cm, 6 cm, 7 cm, 8 cm, 9 cm, 10 cm, 15 cm, 20 cm, 25 cm, 30 cm, 35 cm, 40 cm within the biceps muscle (biceps brachii), the brachialis muscle, the brachioradialus muscle, the triceps muscle (triceps brachii), the deltoid muscle and the pectoral muscles. For example, 1 to 100, or any amount therebetween, injection sites, spaced apart by about 1 mm to about 50 cm, or any amount therebetween, for example, injection sites spaced apart by about 1 mm, 2.5 mm, 5 mm, 0.75 mm, 1 cm, 1.5 cm, 2 cm, 3 cm, 4 cm, 5 cm, 6 cm, 7 cm, 8 cm, 9 cm, 10 cm, 15 cm, 20 cm, 25 cm, 30 cm, 35 cm, 40 cm, 45 cm may be used for injection within the hamstrings, such as the biceps femoris, semitendinosus and semimembranosus muscles of the hamstrings; the quadriceps, including the rectus femoris, vastus lateralis, vastus medialis and vastus intermedius muscles of the quadriceps; the calves, including the gastrocnemius, tibialis anterior, and the soleus muscles of the calves; and the gluteus maximus, gluteus medius and gluteus minimus of the buttocks.

The volume of the composition injected at each location within a muscle may vary depending on the muscle injected, the number of locations injected and/or the desired effect. For example, the volume of the composition injected at each location can be in the range of approximately 0.01 cc/kg of body weight to approximately 6.0 cc/kg of body weight, or any amount therebetween, for example, from approximately 0.01 cc to approximately 5.0 cc/kg of body weight, from approximately 0.01 cc to approximately 4.0 cc/kg of body weight, from approximately 0.01 cc to approximately 3.0 cc/kg of body weight, from approximately 0.01 cc to approximately 2.0 cc/kg of body weight, from approximately 0.01 cc to approximately 1 cc/kg of body weight, or from approximately 0.01 cc to approximately 0.5 cc/kg of body weight, or any amount therebetween. For example, from about 0.01, 0.05, 0.08, 0.1, 0.2, 0.3, 0.4, 0.5, 0.6, 0.7, 0.8, 0.9, 1.0, 1.1, 1.2, 1.4, 1.5, 1.6, 1.7, 1.8, 2.0, 2.1, 2.2, 2.5, 2.8, 2.9, 3.0, 3.1, 3.5, 3.6, 3.7, 3.8, 4.0, 4.2, 4.3, 4.5, 4.8, 4.9, 5.0, 5.2, 5.4, 5.5, 5.7, 5.8, 5.9, 6.0 cc/kg of body weight, or any amount therebetween, may be injected per location within a muscle.

Injections comprising the same amount, or different amounts, of HA composition, may also be repeated on a periodic basis, for example, a repeat treatment every month, every 2 months, every 3 months, every 4 months, every 6 months, every 8 months, every 12 months, every 15 months, every 18 months, every 2 years, every 2.5 years, or a combination thereof, as desired. Repeat treatments may be performed to either maintain the muscular volume or progressively augment the muscular volume over time.

The injections of the composition comprising HA and/or its derivatives thereof may be done with the assistance of an ultrasound machine, or any other method for imaging muscle that is known in the art, to visualize the muscle of interest while injecting the composition. While visualizing the muscle using ultrasound or any other suitable method known in the art, the HA composition may be injected using real-time guidance to guide the exact location of injection of the HA composition.

The present disclosure contemplates intramuscular injection of the composition described herein using a cannula, needle, syringe or any other instrument for injection of a solution into a human. The length of the cannula, needle or other instrument used will vary depending on the injection site and the particular person to be injected as the thickness of the fat pad and skin over a specific injection site will vary to a great extent between individuals and injection sites. Intramuscular injections must go into the muscle below the subcutaneous layer, therefore a relatively long instrument will be used to ensure the composition is injected into the muscle. For example, but without limitation, the length of the needle or cannula may vary between approximately 2 cm to approximately 10 cm in length, or any length therebetween. The gauge of the needle will vary depending on the viscosity of the injected HA composition, and the rate of injection desired. The chosen cannula or needle should generally be the smallest gauge needle that will allow for suitable injection rates of the HA composition, in order to minimize patient discomfort. For example, but without limitation, the gauge of the needle or cannula may vary between a 14-gauge needle or cannula and a 30-gauge needle or cannula, and any sized gauge needle or cannula therebetween.

The amount of the composition injected will be dependent on the injection site and desired effect. Generally, but without limitation, approximately 0.01 cc/kg of body weight to approximately 6.0 cc/kg of body weight of the composition will be injected per muscle of a person, or any amount therebetween, for example, from approximately 0.01 cc to approximately 5.0 cc/kg of body weight, from approximately 0.01 cc to approximately 4.0 cc/kg of body weight, from approximately 0.01 cc to approximately 3.0 cc/kg of body weight, from approximately 0.01 cc to approximately 2.0 cc/kg of body weight, from approximately 0.01 cc to approximately 1.0 cc/kg of body weight, or from approximately 0.01 cc to approximately 0.5 cc/kg of body weight, or any amount therebetween. For example, from about 0.01, 0.05, 0.08, 0.1, 0.2, 0.3, 0.4, 0.5, 0.6, 0.7, 0.8, 0.9, 1.0, 1.1, 1.2, 1.4, 1.5, 1.6, 1.7, 1.8, 2.0, 2.1, 2.2, 2.5, 2.8, 2.9, 3.0, 3.1, 3.5, 3.6, 3.7, 3.8, 4.0, 4.2, 4.3, 4.5, 4.8, 4.9, 5.0, 5.2, 5.4, 5.5, 5.7, 5.8, 5.9, 6.0 cc/kg of body weight, or any amount therebetween, may be injected per muscle of a person.

As an example, which is not to be considered limiting, for injection into a muscle of the arm, such as the triceps or the biceps, it is contemplated that approximately 0.01 cc/kg of body weight to approximately 2.0 cc/kg of body weight of the composition may be injected per triceps or biceps muscle, or any amount therebetween, for example, from approximately 0.01 cc/kg of body weight to approximately 1.8 cc/kg of body weight in total per triceps or biceps muscle, from approximately 0.01 cc/kg of body weight to approximately 1.7 cc/kg of body weight in total per triceps or biceps muscle, from approximately 0.01 cc/kg of body weight to approximately 1.6 cc/kg of body weight in total per triceps or biceps muscle, from approximately 0.01 cc/kg of body weight to approximately 1.5 cc/kg of body weight in total per triceps or biceps muscle, or any amount therebetween. If multiple injection sites are used along the muscle, then the amount of the HA composition to be injected may be divided as required between injection sites and locations at the injection sites.

If injecting into the brachialis muscle of the arm, it is contemplated, for example, without limitation, that approximately 0.01 cc/kg of body weight to approximately 1.5 cc/kg of body weight of the composition may be injected per brachialis muscle, or any amount therebetween, for example, from approximately 0.01 cc/kg of body weight to approximately 1.4 cc/kg of body weight in total per brachialis muscle, from approximately 0.01 cc/kg of body weight to approximately 1.3 cc/kg of body weight in total per brachialis muscle, from approximately 0.01 cc/kg of body weight to approximately 1.2 cc/kg of body weight in total per brachialis muscle, from approximately 0.01 cc/kg of body weight to approximately 1.0 cc/kg of body weight in total per brachialis muscle, or any amount therebetween. If multiple injection sites are used along the muscle, then the amount of the HA composition to be injected may be divided as required between injection sites and locations at the injection sites.

As a further example, which is not to be considered limiting, for injection into a brachioradialis muscle, it is contemplated that approximately 0.01 cc/kg of body weight to approximately 0.8 cc/kg of body weight of the composition may be injected per brachioradialis muscle, or any amount therebetween, for example, from approximately 0.01 cc/kg of body weight to approximately 0.75 cc/kg of body weight in total per brachioradialis muscle, from approximately 0.01 cc/kg of body weight to approximately 0.7 cc/kg of body weight in total per brachioradialis muscle, from approximately 0.01 cc/kg of body weight to approximately 0.6 cc/kg of body weight in total per brachioradialis muscle, from approximately 0.01 cc/kg of body weight to approximately 0.5 cc/kg of body weight in total per brachioradialis muscle, or any amount therebetween. If multiple injection sites are used along the muscle, then the amount of the HA composition to be injected may be divided as required between injection sites and locations at the injection sites.

For injection into the superficial compartment wrist flexor muscle, for example, which is not to be considered limiting, approximately 0.01 cc/kg of body weight to approximately 0.8 cc/kg of body weight may be injected per superficial wrist flexor group, or any amount therebetween, for example, from approximately 0.01 cc/kg of body weight to approximately 0.75 cc/kg of body weight in total per superficial wrist flexor group, from approximately 0.01 cc/kg of body weight to approximately 0.7 cc/kg of body weight in total per superficial wrist flexor group, from approximately 0.01 cc/kg of body weight to approximately 0.6 cc/kg of body weight in total per superficial wrist flexor group, from approximately 0.01 cc/kg of body weight to approximately 0.5 cc/kg of body weight in total per superficial wrist flexor group, or any amount therebetween. If multiple injection sites are used along the superficial wrist flexor group, then the amount of the HA composition to be injected may be divided as required between injection sites and locations at the injection sites.

Another example, which is not to be considered limiting, is provided for injection into the calf muscles of the leg, such as the lateral gastrocnemius, the medial gastrocnemius, or the soleus muscles. Approximately 0.01 cc/kg of body weight to approximately 1.3 cc/kg of body weight may be injected per lateral gastrocnemius muscle, or any amount therebetween, for example, from approximately 0.01 cc/kg of body weight to approximately 1.2 cc/kg of body weight in total per lateral gastrocnemius muscle, from approximately 0.01 cc/kg of body weight to approximately 1.1 cc/kg of body weight in total per lateral gastrocnemius muscle, from approximately 0.01 cc/kg of body weight to approximately 1.0 cc/kg of body weight in total per lateral gastrocnemius muscle, or any amount therebetween. Approximately 0.01 cc/kg of body weight to approximately 1.3 cc/kg of body weight may be injected per medial gastrocnemius muscle, or any amount therebetween, for example, from approximately 0.01 cc/kg of body weight to approximately 0.6 cc/kg of body weight in total per medial gastrocnemius muscle, from approximately 0.01 cc/kg of body weight to approximately 0.5 cc/kg of body weight in total per medial gastrocnemius muscle, or any amount therebetween. Approximately 0.01 cc/kg of body weight to approximately 3.2 cc/kg of body weight may be injected per soleus muscle, or any amount therebetween, for example, from approximately 0.01 cc/kg of body weight to approximately 3.1 cc/kg of body weight in total per soleus muscle, from approximately 0.01 cc/kg of body weight to approximately 3.0 cc/kg of body weight in total per soleus muscle, or any amount therebetween. If multiple injection sites are used along the muscle, then the amount of the HA composition to be injected may be divided as required between injection sites and locations at the injection sites.

As a further non-limiting example, it is contemplated that approximately 0.01 cc/kg of body weight to approximately 5.0 cc/kg of body weight of the composition may be injected per quadricep muscle, or any amount therebetween, for example, from approximately 0.01 cc/kg of body weight to approximately 4.9 cc/kg of body weight in total per quadricep muscle, from approximately 0.01 cc/kg of body weight to approximately 4.8 cc/kg of body weight in total per quadricep muscle, from approximately 0.01 cc/kg of body weight to approximately 4.7 cc/kg of body weight in total per quadricep muscle, or any amount therebetween, with approximately 0.01 cc/kg of body weight to approximately 1.1 cc/kg of body weight of the composition, for example, injected into the rectus femoris of the quadricep, or any amount therebetween, approximately 0.01 cc/kg of body weight to approximately 2.1 cc/kg of body weight of the composition, for example, injected into the vastus lateralis of the quadriceps, or any amount therebetween, and approximately 0.01 cc/kg of body weight to approximately 1.8 cc/kg of body weight of the composition, for example, injected into the vastus medialis of the quadriceps, or any amount therebetween. If multiple injection sites are used along the muscle, then the amount of the HA composition to be injected may be divided as required between injection sites and locations at the injection sites.

Another example, which is not to be considered limiting, for injection into a hamstring muscle, it is contemplated that approximately 0.01 cc/kg of body weight to approximately 5.6 cc/kg of body weight of the composition may be injected per hamstring muscle, or any amount therebetween, for example, from approximately 0.01 cc/kg of body weight to approximately 5.5 cc/kg of body weight in total per hamstring muscle, from approximately 0.01 cc/kg of body weight to approximately 5.4 cc/kg of body weight in total per hamstring muscle, from approximately 0.01 cc/kg of body weight to approximately 5.3 cc/kg of body weight in total per hamstring muscle, or any amount therebetween, with approximately 0.01 cc/kg of body weight to approximately 2.1 cc/kg of body weight of the composition, for example, injected into the biceps femoris of the hamstring, or any amount therebetween, approximately 0.01 cc/kg of body weight to approximately 2.9 cc/kg of body weight of the composition, for example, injected into the semitendinosis/semimembranosis of the hamstring, or any amount therebetween, and approximately 0.01 cc/kg of body weight to approximately 0.6 cc/kg of body weight of the composition, for example, injected into the gracilis of the hamstring, or any amount therebetween. If multiple injection sites are used along the muscle, then the amount of the HA composition to be injected may be divided as required between injection sites and locations at the injection sites.

For injection into the muscles of the buttocks, such as the gluteus maximus or the gluteus medius, for example, which is not to be considered limiting, approximately 0.01 cc/kg of body weight to approximately 6.0 cc/kg of body weight may be injected per gluteus maximus, or any amount therebetween, for example, from approximately 0.01 cc/kg of body weight to approximately 5.8 cc/kg of body weight in total per gluteus maximus muscle, from approximately 0.01 cc/kg of body weight to approximately 5.7 cc/kg of body weight in total per gluteus maximus muscle, from approximately 0.01 cc/kg of body weight to approximately 5.5 cc/kg of body weight in total per gluteus maximus muscle, or any amount therebetween. If injecting into the gluteus medius, approximately 0.01 cc/kg of body weight to approximately 2.3 cc/kg of body weight may be injected per gluteus medius, or any amount therebetween, for example, from approximately 0.01 cc/kg of body weight to approximately 2.2 cc/kg of body weight in total per gluteus medius muscle, from approximately 0.01 cc/kg of body weight to approximately 2.1 cc/kg of body weight in total per gluteus medius muscle, from approximately 0.01 cc/kg of body weight to approximately 2.0 cc/kg of body weight in total per gluteus medius muscle, or any amount therebetween. If multiple injection sites are used along the muscle, then the amount of the HA composition to be injected may be divided as required between injection sites and locations at the injection sites.

As a further non-limiting example, it is contemplated that approximately 0.01 cc/kg of body weight to approximately 2.3 cc/kg of body weight of the composition may be injected per deltoid muscle, or any amount therebetween, for example, from approximately 0.01 cc/kg of body weight to approximately 2.2 cc/kg of body weight in total per deltoid muscle, from approximately 0.01 cc/kg of body weight to approximately 2.1 cc/kg of body weight in total per deltoid muscle, from approximately 0.01 cc/kg of body weight to approximately 2.0 cc/kg of body weight in total per deltoid muscle, or any amount therebetween. If multiple injection sites are used along the muscle, then the amount of the HA composition to be injected may be divided as required between injection sites and locations at the injection sites.

As a further example, which is not to be considered limiting, for injection into a trapezius muscle, it is contemplated that approximately 0.01 cc/kg of body weight to approximately 2.3 cc/kg of body weight of the composition may be injected per trapezius muscle, or any amount therebetween, for example, from approximately 0.01 cc/kg of body weight to approximately 2.2 cc/kg of body weight in total per trapezius muscle, from approximately 0.01 cc/kg of body weight to approximately 2.1 cc/kg of body weight in total per trapezius muscle, from approximately 0.01 cc/kg of body weight to approximately 2.0 cc/kg of body weight in total per trapezius muscle, or any amount therebetween. If multiple injection sites are used along the muscle, then the amount of the HA composition to be injected may be divided as required between injection sites and locations at the injection sites.

For injection into the pectoralis major muscle, for example, which is not to be considered limiting, approximately 0.01 cc/kg of body weight to approximately 3.8 cc/kg of body weight may be injected per pectoralis major muscle, or any amount therebetween, for example, from approximately 0.01 cc/kg of body weight to approximately 3.6 cc/kg of body weight in total per pectoralis major muscle, from approximately 0.01 cc/kg of body weight to approximately 3.5 cc/kg of body weight in total per pectoralis major muscle, from approximately 0.01 cc/kg of body weight to approximately 3.4 cc/kg of body weight in total per pectoralis major muscle, or any amount therebetween. If multiple injection sites are used along the muscle, then the amount of the HA composition to be injected may be divided as required between injection sites and locations at the injection sites.

For injection into the muscles of the back, such as the latissmus dorsi muscle, for example, which is not to be considered limiting, approximately 0.01 cc/kg of body weight to approximately 4.4 cc/kg of body weight may be injected per latissmus dorsi muscle, or any amount therebetween, for example, from approximately 0.01 cc/kg of body weight to approximately 4.3 cc/kg of body weight in total per latissmus dorsi muscle, from approximately 0.01 cc/kg of body weight to approximately 4.2 cc/kg of body weight in total per latissmus dorsi muscle, from approximately 0.01 cc/kg of body weight to approximately 4.1 cc/kg of body weight in total per latissmus dorsi muscle, or any amount therebetween. If multiple injection sites are used along the muscle, then the amount of the HA composition to be injected may be divided as required between injection sites and locations at the injection sites.

As a further example, which is not to be considered limiting, for injection into a muscle in the abdomen, such as the rectus abdominis muscle, it is contemplated that approximately 0.01 cc/kg of body weight to approximately 0.5 cc/kg of body weight of the composition may be injected per rectus abdominis muscle, or any amount therebetween, for example, from approximately 0.01 cc/kg of body weight to approximately 0.45 cc/kg of body weight in total per rectus abdominis muscle, from approximately 0.01 cc/kg of body weight to approximately 0.4 cc/kg of body weight in total per rectus abdominis muscle, or any amount therebetween. If multiple injection sites are used along the muscle, then the amount of the HA composition to be injected may be divided as required between injection sites and locations at the injection sites.

The volume of the HA composition and/or any derivative thereof may be approximately 0.01% to approximately 25% of the total muscle volume of the muscle to be injected, or any amount therebetween. For example, the volume of the HA composition and/or any derivative thereof may be from about 0.01, 0.02, 0.05, 0.08, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 16.0, 17.0, 18.0, 19.0, 20.0, 21.0, 22.0, 23.0, 24.0% of the total muscle volume of the muscle to be injected. The total volume of muscle injected will vary depending on the desired cosmetic and/or muscle performance effect. The increase in muscular volume of the muscle as compared to the muscular volume prior to injecting the HA composition into the muscle is proportional to the amount of the HA composition injected into the muscle of interest, and may continue to persist in the muscle for approximately 6 months to approximately 2.5 years after the initial injection before being degraded by enzymatic degradation (hyaluronidase) and reaction with reactive oxygen species (for example, superoxide and peroxynitrite).

The methods of the present disclosure therefore further contemplate additional injections of the composition comprising HA into the same muscle following the initial injections. At any time after the initial injection, for example, but without limitation, approximately one week to approximately two and half years or later, or any time therebetween, additional injections into the same muscle may be performed to touch-up the shape or contour of the muscle, to maintain muscle performance, to maintain muscular volume, or to further augment muscular volume. For example, the additional injections may be made approximately 2 months, 3 months, 4 months, 6 months, 9 months, 12 months, 15 months, 18 months, 21 months, 24 months, 26 months, 28 months or 30 months following the initial injection, or any time period therebetween, and repeated thereafter. The amount of the additional injections will vary depending on the amount initially injected, the injection site, the effect that is desired, and/or the amount of the composition that has been resorbed by the person's body. As an indication, approximately 0.01 cc/kg of body weight to approximately 6.0 cc/kg of body weight of the composition may be injected per muscle of a person, or any amount therebetween, following the initial injection.

For those repeat injections done to maintain muscular volume or muscular performance (i.e., no further augmentation of the muscle), the additional injections of the composition comprising HA may be repeated every 1, 2, 3, 6, 12, 18, 24 or 30 months, or any time therebetween. Such maintenance injections may comprise low volume doses, such as, without limitation, doses of approximately 0.1 cc/kg to approximately 1.0 cc/kg of body weight, or any amount therebetween, of the HA composition may be injected into the muscle of interest. For example, the dose of the HA composition and/or any derivative thereof for injection into the muscle of interest may be from about 0.1, 0.2, 0.3, 0.4, 0.5, 0.6, 0.7, 0.8 0.9, 1.0 cc/kg of body weight, or any amount therebetween, per repeat injection. The dose injected and the frequency of the repeat injections may depend on the physical activity of the individual patient. If a patient is more physically active (for example, routinely works-out or routinely strength trains), a lower dose and/or less frequent repeat injections may be desired.

For those repeat injections done to progressively augment the muscle over time (i.e., to achieve a greater muscular volume over time), the additional injections of the composition comprising HA may be done in a step-wise manner. As described above, a volume ranging from approximately 0.1 cc/kg to approximately 6.0 cc/kg of body weight may be initially injected into the muscle of interest. At a time after the initial injection, for example, but without limitation, approximately 1 months to 8 months or later, or any time therebetween, additional injections into the same muscle may be performed to achieve additive effects on the initial injection. For example, injections may be repeated every 1, 2, 3, 4, 5, 6, 7, 8 months, or any time therebetween, after the initial injection, until the desired effect is achieved. Such "progressive augmentation" injections may comprise doses of the HA composition ranging from approximately 0.1 cc/kg to approximately 6.0 cc/kg of body weight, or any amount therebetween. For example, doses from about 0.1, 0.2, 0.3, 0.4, 0.5, 0.6, 0.7, 0.8, 0.9, 1.0, 1.1, 1.2, 1.4, 1.5, 1.6, 1.7, 1.8, 2.0, 2.1, 2.2, 2.5, 2.8, 2.9, 3.0, 3.1, 3.5, 3.6, 3.7, 3.8, 4.0, 4.2, 4.3, 4.5, 4.8, 4.9, 5.0, 5.2, 5.4, 5.5, 5.7, 5.8, 5.9, 6.0 cc/kg of body weight of the HA composition, or any amount therebetween, may be injected per repeat injection, depending on the desired effect.

By injecting the composition comprising HA into a muscle of a person, an increase in muscular volume of the muscle occurs, which increase may be done for cosmetic purposes or to improve muscle function or performance.

As used herein, the term "cosmetic purpose" means that the increase in muscular volume by intramuscular injection of the composition comprising HA is performed to improve the external appearance of the muscle, such as the shape, profile or contour of the muscle or the muscular definition of the muscle.

As used herein, the term "muscle function" or "muscle performance" means the strength of the muscle, which refers to the amount of force the muscle can produce with a single maximal effort, the endurance of the muscle, which refers to the ability of the muscle to sustain repeated contractions against a resistance for an extended period of time, or both maximal effort and endurance.

The muscle function of a person prior to the step of injecting the HA composition can be compared with the muscle function after the step of injecting, for example, from about one week to any desired time period after treatment, for example from about one week to about two years, or any time period therebetween, for example, 2 months, 3 months, 6 months, 9 months, 12 months, 15 months, 18 months, 21 months, or any time period therebetween. The muscle function can be assessed based on a general questionnaire asking a person to rate their muscle strength and muscle endurance, by having the person complete muscle function tests, or both. For example, without limitation, muscle function can be assessed by measuring the power of the muscle. A person's arm muscle function, for example, may be determined by measuring the maximum weight the person is able to lift in a single repetition (i.e., the person's one repetition maximum), by measuring the number of times a person can lift a certain weight during a certain time period, or by measuring the amount of time it takes for a person to lift a certain amount of weights a certain number of times. Other methods known to those skilled in the art may also be used to measure muscle function. For example, isokinetic dynamometry, as described in the art, may be used to quantify muscle strength by assessing dynamic muscle and joint function under specific joint velocity conditions controlled and maintained constant by isokinetic dynamometers.

Muscle function is considered improved if a person's answers to the questionnaire after the step of injecting indicate that the person has more muscle strength and/or endurance in the muscle of interest as compared to before the step of injecting. Muscle function is also considered improved if the person is able to consistently lift more weight in a single repetition, lift a certain weight a greater number of times during a specific time period, or lift a certain amount of weights a certain number of times within a shorter time period than before the step of injecting as compared to before the step of injecting. Further, improvements in force or power measurements with isokinetic dynamometry will also indicate an improvement in muscle function or performance.

Therefore, the present disclosure provides for a method for increasing the muscular volume of a particular muscle of interest in a human, which comprises the intramuscular injection of a composition comprising HA into the muscle of interest. The intramuscular injection results in an increase in the muscular volume of the muscle of interest as compared to the muscular volume of the muscle before it was injected with the composition comprising HA. The increase in muscular volume may be performed for cosmetic purposes and/or to improve the person's muscle function. The muscle injected may be selected from the following group: an arm muscle, a leg muscle, a chest muscle, a back muscle, a buttock muscle, or any other muscle of an individual.

The present disclosure also provides for a method of altering a contour of a muscle of a human that comprises the steps of obtaining an image of the contour of the muscle, determining a new contour of the muscle, injecting a composition comprising HA into one or more than one location of the muscle, for example, two or more, three or more, or four or more locations, to obtain the new contour of the muscle, which results in an alteration of the contour of the muscle. The muscle injected may be selected from the group of an arm muscle, a leg muscle, a chest muscle, a back muscle and a buttock muscle.

As used herein, the term "contour" in relation to a muscle means the outline of the muscle, more specifically, the outline or the line that that defines the outer shape of the muscle. The present disclosure contemplates an alteration of the contour of a person's muscle.

To alter the contour of a muscle, an image of the contour of the muscle is initially obtained. This can be done using any method that can define the contour of the muscle, including, without limitation, photography, magnetic resonance imaging (MRI), ultrasound, physical measurements of the area of the body that contains the muscle of interest such as circumferential measurements of the area, or a combination thereof.

Once the initial image of the contour of the muscle is obtained, a new contour of the muscle can be determined in accordance with the person's desired result. The photograph, MRI image, ultrasound image, physical measurements or combination thereof, of the area of interest are analyzed and the new contour of the muscle is mapped, traced or drawn on the photograph, MRI image, or ultrasound image, or otherwise determined, to depict the new contour of the muscle that is desired.

To alter the contour of the muscle of interest to reflect the desired contour, it may be useful to also physically mark the one or more than one injection sites, for example, the two or more, three or more, or four or more injection sites, on the individual to be injected. The composition comprising HA that is to be injected is as described above.

The methods of the present disclosure also provide for the intramuscular injections of the composition to be done in one or more than one location of a muscle to be injected, for example, two or more, three or more, or four or more locations. The composition comprising HA may be injected at one to about 100 locations, or any amount therebetween, spaced approximately evenly along the muscle fibre of the muscle to be injected for uniform distribution of the HA composition, or at any other locations along the muscle fibre of the muscle, such as concentrated at one or more locations along the muscle, depending on the desired effect. Therefore, the one or more than one, two or more, three or more, or four or more locations of injection will depend on the new contour of the muscle desired and the image of the contour of the muscle initially obtained. For example, without limitation, the composition comprising HA can be injected at one or more than one, two or more, three or more, or four or more locations along the length of the muscle or can be injected at one or more that one, two or more, three or more, or four or more locations that are limited to a specific section of the muscle to increase the muscular volume of that specific section of the muscle.

As described above, the method further contemplates additional injections of the composition comprising HA into the same muscle following the initial injections to touch-up the contour of the muscle or to further augment muscular volume. These additional injections may be done at any time after the initial injection, for example, but without limitation, approximately one week to approximately two and half years or later, or any time therebetween, for example, 2 months, 3 months, 4 months, 6 months, 9 months, 12 months, 15 months, 18 months, 21 months, 24 months, 26 months, 28 months or 30 months following the initial injection, or any time period therebetween. The volume of the composition injected may be between approximately 0.01 cc/kg of body weight to approximately 6 cc/kg of body weight per muscle of a person or any amount therebetween.

For those repeat injections done to maintain the contour of the muscle (i.e., no further augmentation of the muscle), the additional injections of the composition comprising HA may be repeated every 1, 2, 3, 6, 12, 18, 24 or 30 months, or any time therebetween. Such maintenance injections may comprise low volume doses, including, without limitation, doses of approximately 0.1 cc/kg to approximately 1.0 cc/kg of body weight, or any amount therebetween, of the HA composition for injection into the muscle of interest. For example, the dose of the HA composition and/or any derivative thereof for injection into the muscle of interest may be from about 0.1, 0.2, 0.3, 0.4, 0.5, 0.6, 0.7, 0.8 0.9, 1.0 cc/kg of body weight, or any amount therebetween, per repeat injection. The dose injected and the frequency of the repeat injections may depend on the physical activity of the individual patient. If a patient is more physically active (for example, routinely works-out or routinely strength trains), a lower dose and/or less frequent repeat injections may be desired.

For those repeat injections done to progressively augment the contour of the muscle over time, the additional injections of the composition comprising HA may be done in a step-wise manner. As described above, a volume ranging from approximately 0.1 cc/kg to approximately 6.0 cc/kg of body weight may be initially injected into the muscle of interest. At a time after the initial injection, for example, but without limitation, approximately 1 months to 8 months or later, or any time therebetween, additional injections into the same muscle may be performed to achieve additive effects on the initial injection. For example, injections may be repeated every 1, 2, 3, 4, 5, 6, 7 or 8 months, or any time therebetween, until the desired effect is achieved. Such "progressive augmentation" injections may comprise doses of the HA composition ranging from approximately 0.1 cc/kg to approximately 6.0 cc/kg of body weight, or any amount therebetween. For example, from about 0.1, 0.2, 0.3, 0.4, 0.5, 0.6, 0.7, 0.8, 0.9, 1.0, 1.1, 1.2, 1.4, 1.5, 1.6, 1.7, 1.8, 2.0, 2.1, 2.2, 2.5, 2.8, 2.9, 3.0, 3.1, 3.5, 3.6, 3.7, 3.8, 4.0, 4.2, 4.3, 4.5, 4.8, 4.9, 5.0, 5.2, 5.4, 5.5, 5.7, 5.8, 5.9, 6.0 cc/kg of body weight, or any amount therebetween, may be injected per repeat injection, depending on the desired effect.

The present disclosure also provides for a use of a composition comprising HA for increasing muscular volume of a muscle in a human compared to the muscular volume of the muscle in the absence of said composition. The composition comprising HA is as described herein and is for injection into the muscle of the human for cosmetic purposes or for improving the muscle function of the muscle.

The present disclosure also provides for a kit comprising a composition comprising HA and instructions for intramuscular injection of the composition into a muscle in a human.

The present invention will be further illustrated in the following examples.

EXAMPLES

In total, nine healthy patients have been treated with hyaluronic acid for augmentation of select muscles. The treatments were done for either cosmetic purposes, to improve muscle function or performance, or for both cosmetic purposes and to improve muscle function. This resulted in a total of 19 muscle pairs (i.e., bilateral), or 38 individual muscles, being injected with hyaluronic acid. The various heads of the triceps, biceps, deltoid and gastrocnemius are counted as a single muscle. The superficial flexor compartment of the wrist is also considered a single muscle.

None of the patients have experienced complications with the hyaluronic acid treatments. All nine patients had short term follow-ups (i.e., at least at 1 week, 2 weeks, 6 weeks or 8 weeks post-injection) and six of the patients had longer term follow-ups (i.e., greater than one year post-injection). The longest long-term follow-up is currently 28 months.

Example 1. Gluteus Maximus Augmentation—Patient A

A healthy 26 year old female weighing approximately 48 kg, with a height of approximately 165 cm was selected to undergo gluteus maximus augmentation. The patient had no pre-existing medical conditions and consented to the procedure. The patient had been previously injected with 1 cc doses of hyaluronic acid at remote locations and showed no clinical evidence of unfavourable reactions at one year post treatment.

The patient was undressed from the waist down to her underwear and had been instructed to wear a thong undergarment to provide for a completely exposed gluteal surface.

Figure 2A:
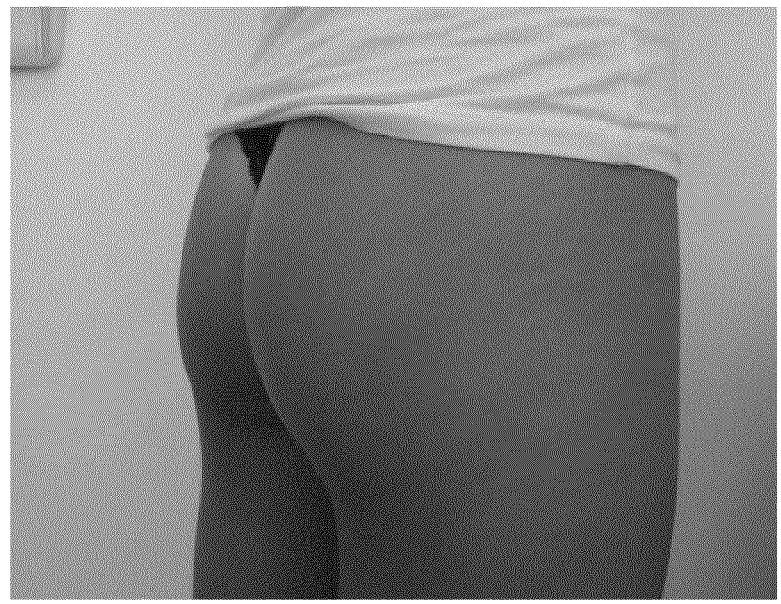
FIG. 2 presents a digital image of a right side view of patient A's buttocks of Example 1 to illustrate the gluteus maximus muscle: (A) prior to injection of the composition comprising HA; and (B) at 8 weeks post-injection of the composition comprising HA.

Digital photographs were taken against a white backdrop at five level angles: posterior median, mid-scapular (right and left), and mid-axillary (right and left). Photographs were then printed on 4"×6" photo paper and 8.5"×11" plain paper (see FIGS. 1A and 2A). Photographs were shown to the patient and the desired clinical augmentation lines were sketched on the plain paper in accordance with the patient's wishes. Injection sites were marked on the plain paper with an "X" and subsequently marked on the corresponding sites on the patient with a black surgical marker.

Thirty minutes prior to the procedure, the patient was given medication in the form of oral oxycodone 10 mg and dimenhydrinate 50 mg in order to palliate any secondary injection pain.

20 cc of cross-linked sodium hyaluronate (Modélis Shape) was prepared for intra-muscular injection by mixing thoroughly but gently with a 2% Xylocaine solution (2 cc sodium hyaluronate was mixed with 0.25 cc 2% Xylocaine solution via 3 cc syringe; the resulting 2.25 cc suspension was transferred into the 3 cc syringe and the process repeated). The resulting suspension was transferred into a syringe and a 25G 1.5" large bore needle was attached and set aside for injection.

The area to be treated was cleaned thoroughly with sterile gauze soaked in Chlorhexidine 2% with 4% isopropyl alcohol. Intramuscular injection was achieved with a perpendicular approach to the skin at the pre-determined "X" injection sites. 1.125 cc was injected at each of 20 injection sites. The needle was advanced through the subcutaneous tissue and pierced through the proximal muscular sheath. Injections were subsequently deposited at locations within the gluteus maximus muscle ranging from about 0.1 cm to about 3 cm from the proximal aspect of the muscular sheath. Negative pressure was applied prior to any injection to assure that the vasculature was not injected. Manual pressure was repetitively applied to injection sites to ensure even distribution of the injectable composition in the local surrounding tissues. Clinical response was observed after each injection. Manual pressure was applied to any bleeding from an injection site and hemostasis was achieved as a contingency for the advancement to the next injection site. The entire process was duplicated for the contralateral side.

Figure 1B:
Figure 2B:
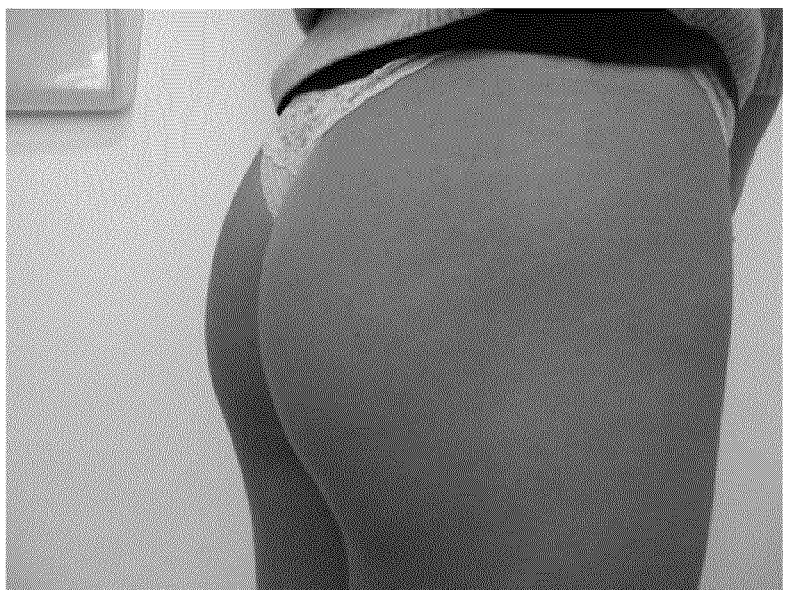

Results:

The patient had a subsequent follow-up at 8 weeks without any signs of complication. Digital photographs were taken in a manner identical to that described above at 8 weeks post-injection (see FIGS. 1B and 2B). Persistent volume augmentation and favourable cosmetic outcome was observed at 8 weeks post-injection.

Example 2. Gluteus Maximus Augmentation—Patient B

A healthy 35 year old female weighing approximately 63 kg, with a height of approximately 170 cm was selected to undergo gluteus maximus augmentation. The patient had no pre-existing medical conditions and consented to the procedure. The patient had been previously injected with 1 cc doses of hyaluronic acid at remote locations and showed no clinical evidence of unfavourable reactions at one year post treatment.

The patient was undressed from the waist down to her underwear and had been instructed to wear a thong undergarment to provide for a completely exposed gluteal surface.

Figure 3A:
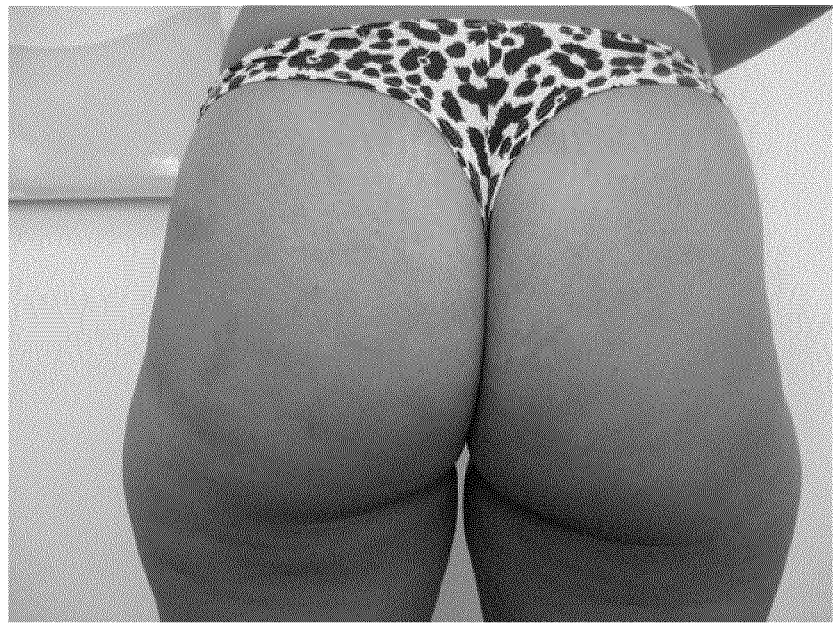
FIG. 3 presents a digital image of a posterior view of patient B's buttocks of Example 2 to illustrate the gluteus maximus muscle: (A) prior to injection of the composition comprising HA; and (B) at 6 months post-injection of the composition comprising HA.

Digital photographs were taken against a white backdrop at five level angles: posterior median, mid-scapular (right and left), and mid-axillary (right and left). Photographs were then printed on 4"×6" photo paper and 8.5"×11" plain paper (see FIG. 3A). Photographs were shown to the patient and the desired clinical augmentation lines were sketched on the plain paper in accordance with the patient's wishes. Injection sites were marked on the plain paper with an "X" and subsequently marked on the corresponding sites on the patient with a black surgical marker.

Thirty minutes prior to the procedure, the patient was given medication in the form of oral oxycodone 10 mg and dimenhydrinate 50 mg in order to palliate any secondary injection pain.

30 cc of cross-linked sodium hyaluronate (Modélis Shape) was prepared for intra-muscular injection as outlined in Example 1.

The area to be treated was cleaned with Chlorhexidine 2% with 4% isopropyl alcohol. Intramuscular injection was achieved with a perpendicular approach to the skin at the pre-determined "X" injection sites. 1.125 cc was injected at each of 30 injection sites. The needle was advanced through the subcutaneous tissue and pierced through the proximal muscular sheath. Injections were subsequently deposited at locations within the gluteus maximus muscle ranging from about 0.1 cm to about 3 cm from the proximal aspect of the muscular sheath. Negative pressure was applied prior to any injection to assure that the vasculature was not injected. Manual pressure was repetitively applied to injection sites to ensure even distribution of the injectable composition in the local surrounding tissues. Clinical response was observed after each injection. Manual pressure was applied to any bleeding from an injection site and hemostasis was achieved as a contingency for the advancement to the next injection site. The entire process was duplicated for the contralateral side.

Figure 3B:

Results:

The patient had subsequent follow-ups at 8 weeks and at 6 months without any signs of complication. Digital photographs were taken in a manner identical to that described above at 6 months post-injection (see FIG. 3B). Persistent volume augmentation and favourable cosmetic outcome was observed at 6 months post-injection.

Example 3. Gastrocnemius Augmentation

A healthy 36 year old male weighing approximately 94 kg, with a height of approximately 180 cm was selected to undergo gastrocnemius augmentation. The patient had no pre-existing medical conditions and consented to the procedure. The patient had been previously injected with 1 cc doses of hyaluronic acid at remote locations and showed no clinical evidence of unfavourable reactions at one year post treatment.

The patient was undressed from the waist down to his undergarments and had been instructed to shave distal legs clean to provide for a completely exposed surface.

Figure 4A:
FIG. 4 presents a digital image of a posterior view of the calves of the male patient of Example 3 to illustrate the gastrocnemius muscle: (A) prior to injection of the composition comprising HA; and (B) at one year post-injection of the composition comprising HA.

Digital photographs were taken against a white backdrop at four level angles: posterior neutral, posterior plantar-flexion, anterior neutral, anterior plantar-flexion. Photographs were then printed on 4"×6" photo paper and 8.5"×11" plain paper (see FIG. 4A). Photographs were shown to the patient and the desired clinical augmentation lines were sketched on the plain paper in accordance with the patient's wishes. Injection sites were marked on the plain paper with an "X" along the inferior border of the two muscle bellies of gastrocnemius and subsequently marked on the corresponding sites on the patient with a black surgical marker.

Thirty minutes prior to the procedure, the patient was given medication in the form of oral oxycodone 10 mg and dimenhydrinate 50 mg in order to palliate any secondary injection pain.

10 cc of cross-linked sodium hyaluronate (Modélis Shape) was prepared for intra-muscular injection as outlined in Example 1.

Figure 4B:

The area to be treated was cleaned thoroughly using Chlorhexidine 2% with 4% isopropyl alcohol. Intramuscular injection was achieved with a perpendicular approach to the skin at the pre-determined "X" injection sites. 1.125 cc was injected at each of 10 injection sites. The needle was advanced through the subcutaneous tissue and pierced through the proximal muscular sheath. Injections were subsequently deposited at locations within the gastrocnemius muscle ranging from about 0.1 cm to about 3 cm from the proximal aspect of the muscular sheath. Negative pressure was applied prior to any injection to assure that the vasculature was not injected. Manual pressure was repetitively applied to injection sites to ensure even distribution of the injectable composition in the local surrounding tissues. Clinical response was observed after each injection. Great care was taken to observe the area for signs of ischemic tissue that might herald the development of compartment syndrome. Manual pressure was applied to any bleeding from an injection site and hemostasis was achieved as a contingency for the advancement to the next injection site. The entire process was duplicated for the contralateral side.
Results:

The patient had subsequent follow-ups at 8, 12, 14, 20, 38, 40, 46, 52, 66, and 90 weeks without any signs of complication. Digital photographs were taken in a manner identical to that described above at 52 weeks (1 year) post-injection (see FIG. 4B). Persistent volume augmentation and favourable cosmetic outcome was observed at 90 weeks post-injection.

Example 4. Triceps Augmentation

A healthy 36 year old male weighing approximately 94 kg, with a height of approximately 180 cm was selected to undergo triceps augmentation. The subject had no pre-existing medical conditions and consented to the procedure. The patient had been previously injected with 1 cc doses of hyaluronic acid at remote locations and showed no clinical evidence of unfavourable reactions at one year post treatment.

Figure 5A:
FIG. 5 presents a digital image of the male patient's arm of Example 4 in a flexed position to illustrate the biceps and triceps muscles: (A) prior to injection of the composition comprising HA; and (B) at 2 weeks post-injection of the composition comprising HA into the biceps muscle and at 14 weeks post-injection of the composition comprising HA into the triceps muscle.

The patient was undressed from the waist up. Digital photographs were taken against a white backdrop at four level angles for each arm: posterior flexion, posterior extension, anterior flexion, and anterior extension. Photographs were then printed on 4"×6" photo paper and 8.5"×11" plain paper (see FIG. 5A). Photographs were shown to the patient and the desired clinical augmentation lines were sketched on the plain paper in accordance with the patient's wishes. Five to seven injection sites were marked on the plain paper with an "X" along the lateral and long heads of the triceps of both arms and subsequently marked on the corresponding sites on the patient with a black surgical marker.

Thirty minutes prior to the procedure, the patient was given medication in the form of oral oxycodone 10 mg and dimenhydrinate 50 mg in order to palliate any secondary injection pain.

15 cc of cross-linked sodium hyaluronate (Modélis Shape) was prepared for intra-muscular injection as outlined in Example 1.

Figure 5B:
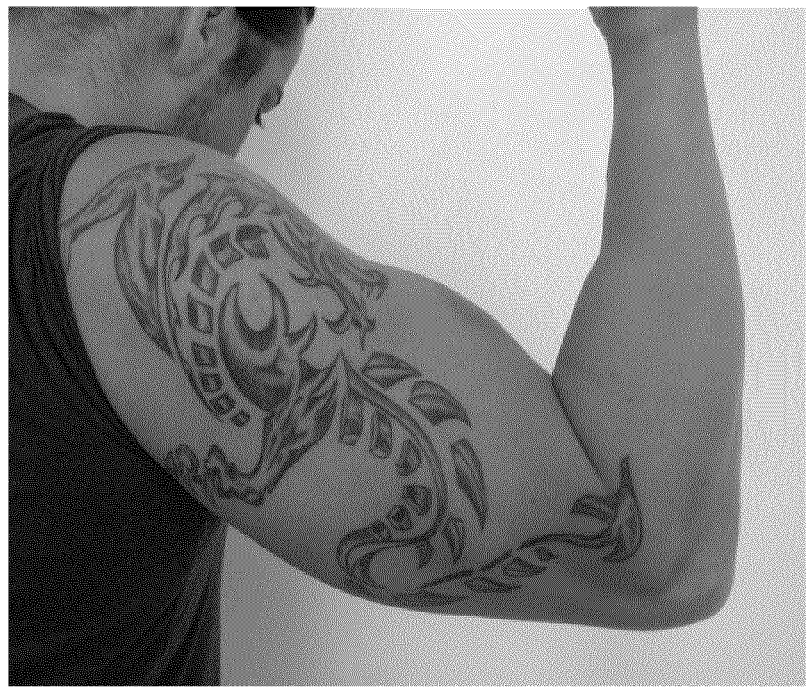

The treatment area was cleaned thoroughly using Chlorhexidine 2% with 4% isopropyl alcohol. Intramuscular injection was achieved with a perpendicular approach to the skin at the pre-determined "X" injection sites. Approximately 16.875 cc was distributed in total by injection between each of the pre-determined triceps injection sites; aliquot volumes at each location within the muscle were based on the desired cosmetic outcome. The needle was advanced through the subcutaneous tissue and pierced through the proximal muscular sheath. Injections were subsequently deposited at locations within the triceps muscle ranging from about 0.1 cm to about 3 cm from the proximal aspect of the muscular sheath. Negative pressure was applied prior to any injection to assure that the vasculature was not injected. Manual pressure was repetitively applied to injection sites to ensure even distribution of the injectable composition in the local surrounding tissues. Clinical response was observed after each injection. Manual pressure was applied to any bleeding from an injection site and hemostasis was achieved as a contingency for the advancement to the next injection site. The entire process was duplicated for the contralateral side.
Results:

The patient had subsequent follow-ups 8, 12, 14, 20, 38, 40, 46, 52, 66, and 90 weeks without any signs of complication. Digital photographs were taken in a manner identical to that described above at 14 weeks post-injection (FIG. 5B). Persistent volume augmentation and favourable cosmetic outcome was observed at 90 weeks post-injection.

Example 5. Biceps Augmentation

A healthy 36 year old male weighing approximately 94 kg, with a height of approximately 180 cm was selected to undergo biceps augmentation. The subject had no pre-existing medical conditions and consented to the procedure. The patient had been previously injected with 1 cc doses of hyaluronic acid at remote locations and showed no clinical evidence of unfavourable reactions at one year post treatment.

The patient was undressed from the waist up. Digital photographs were taken against a white backdrop at four level angles for each arm: posterior flexion, posterior extension, anterior flexion, and anterior extension. Photographs were then printed on 4"×6" photo paper and 8.5"×11" plain paper (see FIG. 5A). Photographs were shown to the patient and the desired clinical augmentation lines were sketched on the plain paper in accordance with the patient's wishes. Injection sites were marked on the plain paper with an "X" along the short and long heads of the biceps of both arms and subsequently marked on the corresponding sites on the patient with a black surgical marker. Three to five injection sites were marked per bicep head depending on the corresponding head length and desired muscular enhancement.

Thirty minutes prior to the procedure, the patient was given medication in the form of oral oxycodone 10 mg and dimenhydrinate 50 mg in order to palliate any secondary injection pain.

10 cc of cross-linked sodium hyaluronate (Modélis Shape) was prepared for intra-muscular injection as outlined in Example 1.

The treatment area was cleaned thoroughly using Chlorhexidine 2% with 4% isopropyl alcohol. Intramuscular injection was achieved with a perpendicular approach to the skin at the pre-determined "X" injection sites. Approximately 11.25 cc was distributed in total by injection between each of the pre-determined biceps injection sites; aliquot volumes at each location within the muscle were based on the desired cosmetic outcome. Negative pressure was applied prior to any injection to assure that the vasculature was not injected. Manual pressure was repetitively applied to injection sites to ensure even distribution of the injectable composition in the local surrounding tissues. Clinical response was observed after each injection. Manual pressure was applied to any bleeding from an injection site and hemostasis was achieved as a contingency for the advancement to the next injection site. The entire process was duplicated for the contralateral side.

Results:

The patient had subsequent follow-ups at 2, 8, 26, 28, 34, 40, 54, and 78 weeks without any signs of complication. Digital photographs were taken in a manner identical to that described above at 2 weeks post-injection (see FIG. 5B). Persistent volume augmentation and favourable cosmetic outcome was observed at 78 weeks post-injection.

Example 6. Brachioradialis and Wrist Flexor Compartment Augmentation

A healthy 36 year old male weighing approximately 94 kg, with a height of approximately 180 cm was selected to undergo brachoradialis augmentation. The patient had no pre-existing medical conditions and consented to the procedure. The patient had been previously injected with 1 cc doses of hyaluronic acid at remote locations and showed no clinical evidence of unfavourable reactions at one year post treatment.

Figure 6A:
FIG. 6 presents a digital image of the male patient's arm of Example 4 in a flexed position to illustrate the brachioradialis muscle and superficial wrist flexors: (A) prior to injection of the composition comprising HA; and (B) at 8 weeks post-injection of the composition comprising HA.

The patient was undressed from the waist up. Digital photographs were taken against a white backdrop at four level angles for each arm: dorsal flexion, dorsal extension, palmar flexion, and palmar extension. Photographs were then printed on 4"×6" photo paper and 8.5"×11" plain paper (see FIG. 6A). Photographs were shown to the patient and the desired clinical augmentation lines were sketched on the plain paper in accordance with the patient's wishes. Injection sites were marked on the plain paper with an "X" along the brachioradialis and wrist flexor compartments of both arms and subsequently marked on the corresponding sites on the patient with a black surgical marker. Four injection sites were marked per brachioradialis and three sites were marked per wrist flexor compartment.

Thirty minutes prior to the procedure, the patient was given medication in the form of oral oxycodone 10 mg and dimenhydrinate 50 mg in order to palliate any secondary injection pain.

5 cc (for brachioradialis) and 3 cc (for wrist flexor compartment) of cross-linked sodium hyaluronate (Modélis Shape) was prepared for intra-muscular injection as outlined in Example 1.

The area for treatment was cleaned thoroughly using Chlorhexidine 2% with 4% isopropyl alcohol. Intramuscular injection was achieved with a perpendicular approach to the skin at the pre-determined "X" injection sites. Approximately 5.625 cc of the HA composition was distributed in total by injection between each of the pre-determined brachioradialis injection sites, and 3.375 cc of the HA composition was distributed in total by injection between each of the forearm wrist flexor compartment injection sites; aliquot volumes at each location within the muscles were based on the desired cosmetic outcome. Negative pressure was applied prior to any injection to assure that the vasculature was not injected. Manual pressure was repetitively applied to injection sites to ensure even distribution of the injectable composition in the local surrounding tissues. Clinical response was observed after each injection. Great care was taken to observe the area for signs of ischemic tissue that might herald the development of compartment syndrome. Manual pressure was applied to any bleeding from an injection site and hemostasis was achieved as a contingency for the advancement to the next injection site. The entire process was duplicated for the contralateral side.

Figure 6B:

Results:

The patient had subsequent follow-ups at 2, 8, 14, 28, and 52 weeks without any signs of complication. Digital photographs were taken in a manner identical to that described above at 8 weeks post-injection (see FIG. 6B). Persistent volume augmentation and favourable cosmetic outcome was observed at 52 weeks post-injection.

Example 7. Deltoid Augmentation

A healthy 36 year old male weighing approximately 94 kg, with a height of approximately 180 cm was selected to undergo deltoid augmentation. The patient had no pre-existing medical conditions and consented to the procedure. The patient had been previously injected with 1 cc doses of hyaluronic acid at remote locations and showed no clinical evidence of unfavourable reactions at one year post treatment.

The patient was undressed from the waist up. Digital photographs were taken against a white backdrop at three level angles for each shoulder: anterior neutral, posterior neutral, and lateral flexion. Photographs were then printed on 4"×6" photo paper and 8.5"×11" plain paper. Photographs were shown to the patient and the desired clinical augmentation lines were sketched on the plain paper in accordance with the patient's wishes. Injection sites were marked on the plain paper with an "X" along the anterior, middle, and posterior heads of the deltoids of both arms and subsequently marked on the corresponding sites on the patient with a black surgical marker. Three to five injection sites were marked per head depending on the corresponding head length and desired muscular enhancement.

Thirty minutes prior to the procedure, the patient was given medication in the form of oral oxycodone 10 mg and dimenhydrinate 50 mg in order to palliate any secondary injection pain.

10 cc of cross-linked sodium hyaluronate (Modélis Shape) was prepared for intra-muscular injection as outlined in Example 1.

The area for treatment was cleaned thoroughly using Chlorhexidine 2% with 4% isopropyl alcohol. Intramuscular injection was achieved with a perpendicular approach to the skin at the pre-determined "X" injection sites. 11.125 cc of the HA composition was injected in total by distributing between each of the pre-determined deltoid injection sites. The needle was advanced through the subcutaneous tissue and pierced through the proximal muscular sheath. Injections were subsequently deposited at locations within the deltoid muscle ranging from about 0.1 cm to about 3 cm from the proximal aspect of the muscular sheath. Negative pressure was applied prior to any injection to assure that the vasculature was not injected. Manual pressure was repetitively applied to injection sites to ensure even distribution of the injectable composition in the local surrounding tissues. Clinical response was observed after each injection. Manual pressure was applied to any bleeding from an injection site and hemostasis was achieved as a contingency for the advancement to the next injection site. The entire process was duplicated for the contralateral side.

Results:

The patient had subsequent follow-ups at 2, 8, 14, 28, and 52 weeks without any signs of complication. Persistent volume augmentation and favourable cosmetic outcome was observed at 52 weeks post-injection.

Example 8. Pectoralis Major Augmentation

A healthy 36 year old male weighing approximately 94 kg, with a height of approximately 180 cm was selected to undergo pectoralis major augmentation. The patient had no pre-existing medical conditions and consented to the procedure. The patient had been previously injected with 1 cc doses of hyaluronic acid at remote locations and showed no clinical evidence of unfavourable reactions at one year post treatment.

Figure 7A:
FIG. 7 presents a digital image of a side view of the chest of the male patient of Example 7 to illustrate the pectoralis major muscle: (A) prior to injection of the composition comprising HA; and (B) at 6 months post-injection of the composition comprising HA.

The patient was undressed from the waist up. Digital photographs were taken against a white backdrop at five level angles: mid-sternal, mid-clavicular (left and right), and mid-axiallary (left-right). Photographs were then printed on 4"×6" photo paper and 8.5"×11" plain paper (see FIG. 7A). Photographs were shown to the patient and the desired clinical augmentation lines were sketched on the plain paper in accordance with the patient's wishes. Injection sites were marked on the plain paper with an "X" and subsequently marked on the corresponding sites on the patient with a black surgical marker. Five injection sites were marked per pectoralis.

Thirty minutes prior to the procedure, the patient was given medication in the form of oral oxycodone 10 mg and dimenhydrinate 50 mg in order to palliate any secondary injection pain.

10 cc of cross-linked sodium hyaluronate (Modélis Shape) was prepared for intra-muscular injection as outlined in Example 1.

The treatment area was cleaned thoroughly using Chlorhexidine 2% with 4% isopropyl alcohol. Intramuscular injection was achieved with a perpendicular approach to the skin at the pre-determined "X" injection sites. Approximately 11.25 cc of the HA composition was distributed in total by injection between each of the pre-determined pectoralis injection sites; aliquot volumes at each location within the pectoralis major muscle were based on the desired cosmetic outcome. The needle was advanced through the subcutaneous tissue and pierced through the proximal muscular sheath. Injections were subsequently deposited at locations within the deltoid muscle ranging from about 0.1 cm to about 3 cm from the proximal aspect of the muscular sheath. Negative pressure was applied prior to any injection to assure that the vasculature was not injected. Manual pressure was repetitively applied to injection sites to ensure even distribution of the injectable composition in the local surrounding tissues. Clinical response was observed after each injection. Manual pressure was applied to any bleeding from an injection site and hemostasis was achieved as a contingency for the advancement to the next injection site. The entire process was duplicated for the contralateral side.

Figure 7B:
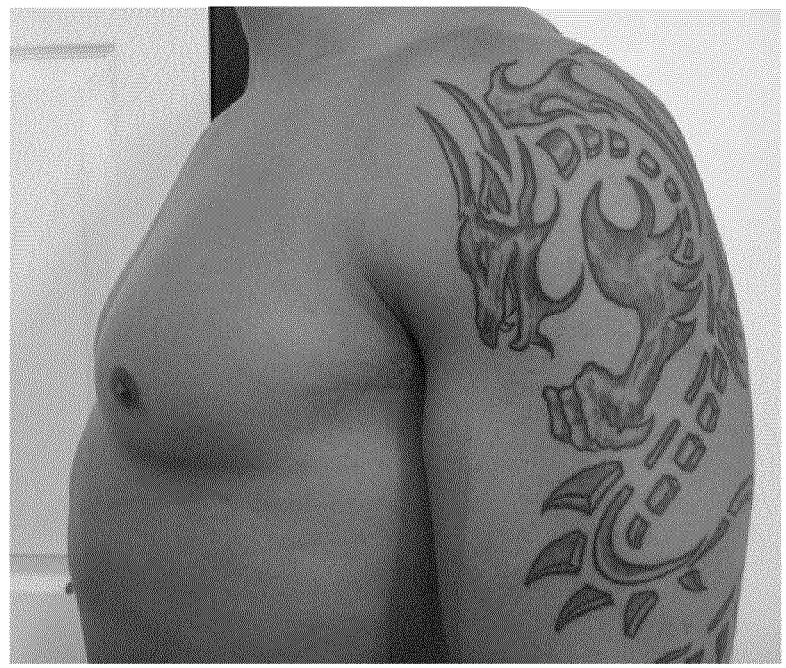

Results:

The patient had subsequent follow-ups at 6, 12, 26, and 50 weeks without any signs of complication. Digital photographs were taken in a manner identical to that described above at 6 months post-injection (see FIG. 7B). Persistent volume augmentation and favourable cosmetic outcome was observed at 50 weeks post-injection.

Example 9. Increase in Muscular Volume and Muscular Function Following HA Injection Patient 1 underwent intramuscular hyaluronic acid injection in multiple muscles at varying dates, including the deltoid, biceps, triceps, medial and lateral heads of gastrocnemius, superficial wrist flexor group, brachioradialis, pectoralis major, and gluteus maximus. Patient 1 was an active weight trainer prior to hyaluronic acid injection and had reached a plateau years ago with no additional size or strength gains despite rigorous training.

Following hyaluronic acid injection, a multisequence post contrast MRI was obtained through the right deltoid, biceps, and triceps muscles. The deltoid muscle had been injected 12 months prior to the MRI, while the biceps muscle had been injected 18 months prior to the MRI, and the triceps was injected 21 months prior to the MRI. Size measurements of the deltoid, biceps and triceps muscles were also obtained following hyaluronic acid injection.

Figure 8A:
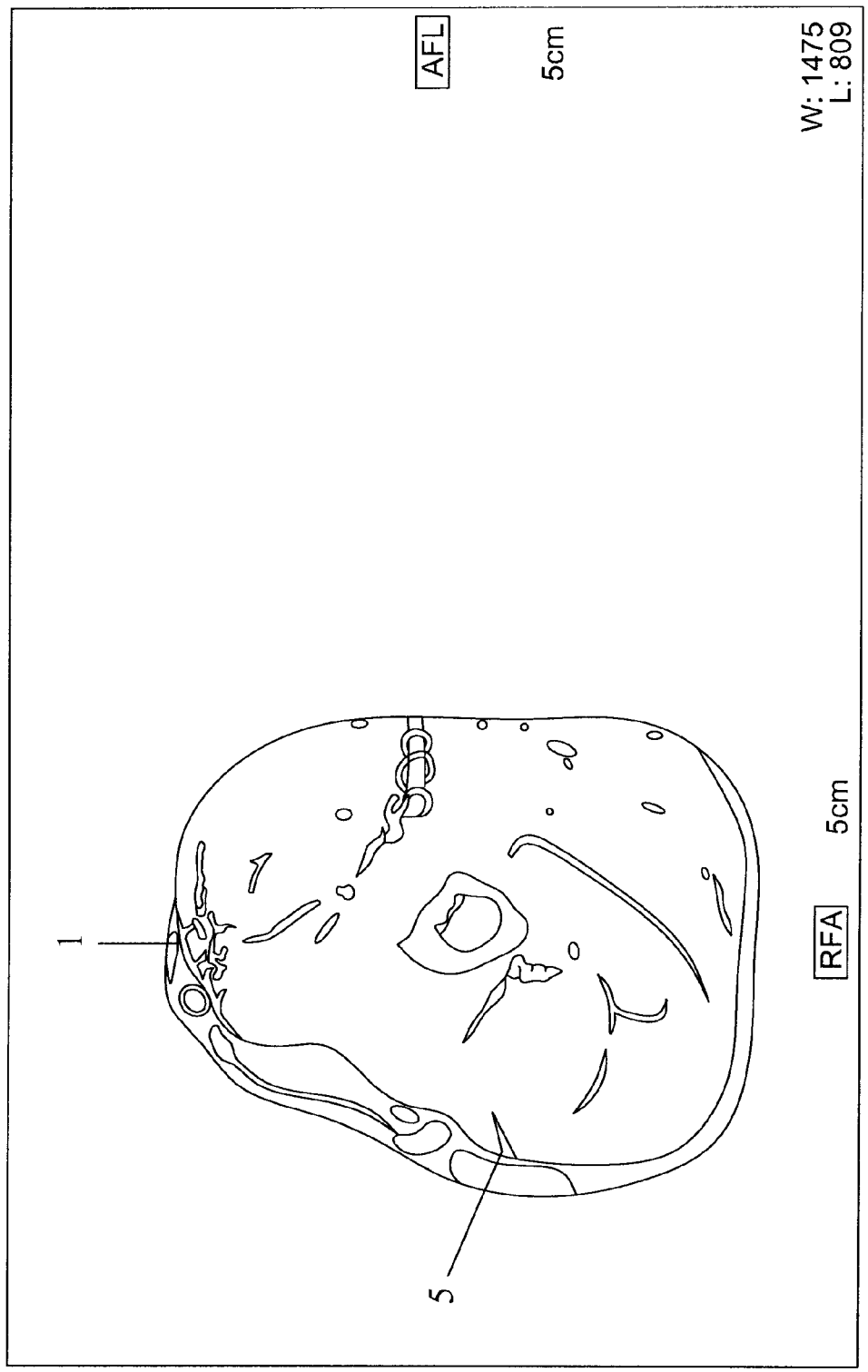
FIG. 8 presents a digital magnetic resonance image of a T2 fat saturated axial image of: (A) the biceps- and triceps-injected muscles 18 months post-injection and 21 months post-injection, respectively; and (B) the deltoid-injected muscle 12 months post-injection.
Figure 8B:
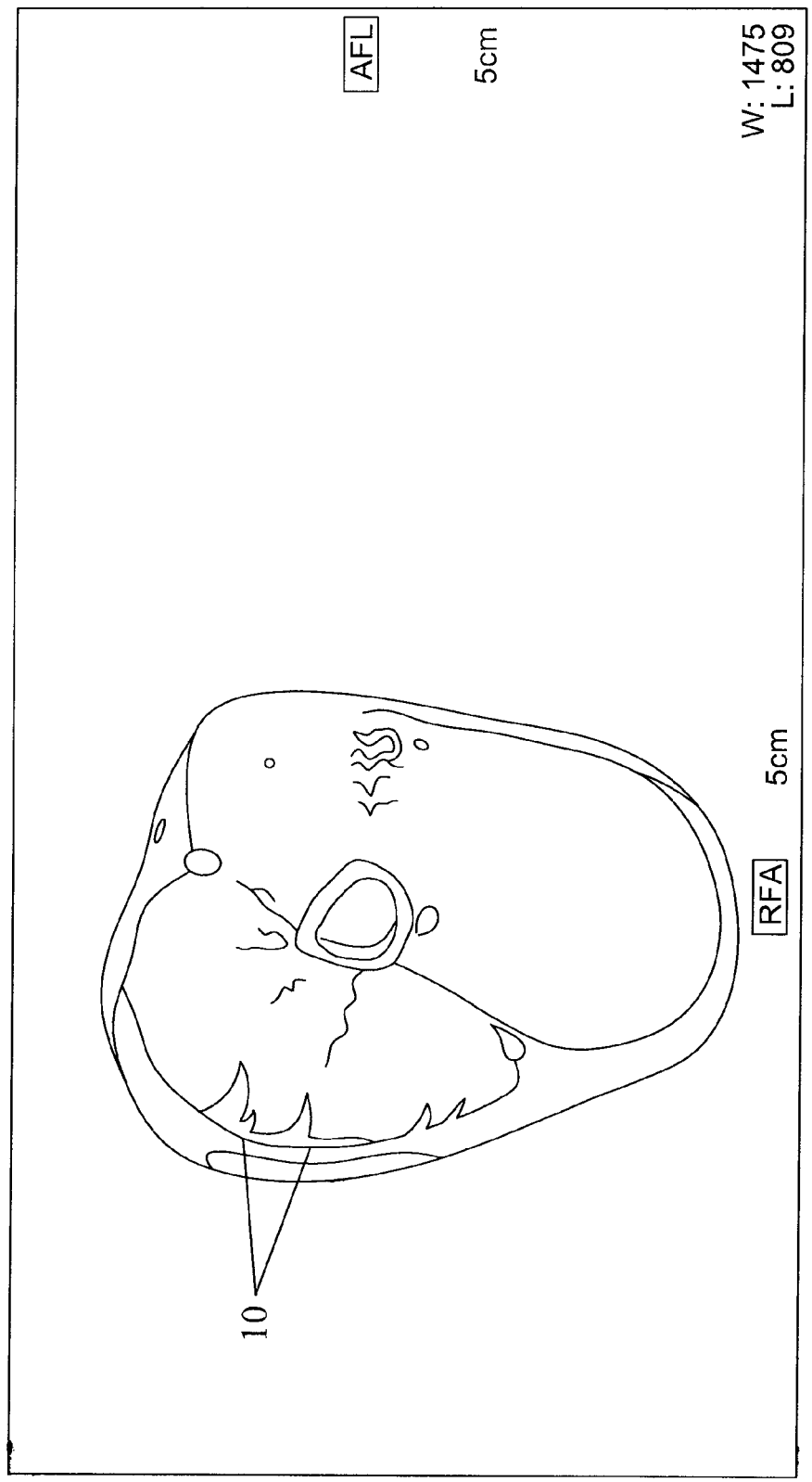
Figure 9:
FIG. 9 presents a digital magnetic resonance image of a T1 fat saturated post-contrast axial image of the deltoid-injected muscle 12 months post-injection.

Results:

The MRI imaging shows residual hyaluronic acid in all three muscles as a high signal on T2 (due to water content). The hyaluronic acid, shown as reference numerals 1 and 5 in FIG. 8(A) and reference number 10 in FIG. 8(B), is seen to insinuate through the muscle fibers in a feathery pattern with a thin rim also tracking along the sheath (see FIGS. 8(A) and 8(B)). Post contrast T1 fat saturated images demonstrate a mild similar feathery enhancement, shown as reference numeral 15 in FIG. 9. Most remaining HA was localized at the superficial or outward facing muscular edge.

No negative reactions were visualized. There are no large spheres of hyaluronic acid with peripheral enhancement that would indicate an abnormal foreign body granulomatous reaction. This is in keeping with the patient's favorable cosmetic outcome with no nodularity, pain, or abnormal functioning.

The amount of residual hyaluronic acid was greatest in the deltoid, followed by the biceps, with a trace of residual product in the triceps; i.e., greater amounts of HA were observed in the more recently injected muscles. Thus, these results correlate with the injection dates, and while not wishing to be bound by theory, suggest a progressive gradual natural enzymatic/free radical degradation of the product by hyaluronidase.

As shown in Table 1, the patient had significant gains in muscle size following injection, demonstrating an increase in muscular volume. This gain in size was maintained over time (21 months in the triceps muscle; last test date).

TABLE 1

Increase in Muscular Volume Following HA Injection

| Muscle | Time of Measurement | Measurement (inches) |
|---|---|---|
| Arm—biceps & triceps | Pre-injection* | 15 |
| | 6 Weeks Post-biceps injection** | 18 |
| | 18 Weeks Post-triceps injection** | |
| | 12 Months Post-biceps injection** | 18 |
| | 15 Months Post-triceps injection** | |
| | 18 Months Post-biceps injection** | 18 |
| | 21 Months Post-triceps injection** | |
| | 25 Months Post-biceps injection** | 18 |
| | 28 Months Post-triceps injection** | |
| Chest | Pre-injection | 41 |
| | 6 Weeks Post-injection | 45 |
| | 12 Months Post-injection | 47 |
| | 19 Months Post-injection | 47 |
| Calves | Pre-injection | 14 |
| | 6 Weeks Post-injection | 15 |
| | 12 Months Post-injection | 15 |
| | 19 Months Post-injection | 15 |

*"Pre-injection" refers to the time prior to any injection of the composition comprising HA into the biceps or triceps muscles.
**There is a constant 12 week difference between the triceps and biceps post-injection time frames as the triceps were injected with the composition comprising HA 12 weeks (3 months) prior to the biceps injection. Therefore, "Post injection" refers to a time after both biceps and triceps were injected, and each post injection time point is relative to the injection time of the respective muscle injected.

After being at a plateau in strength for over a decade, patient 1 also experienced significant strength gains following injection (see Table 2), illustrating an increase in muscle function with HA injection.

TABLE 2

Increase in Muscular Function Following HA Injection

| Muscle | Time of Measurement | Muscle Function x10 reps | x4 reps |
|---|---|---|---|
| Biceps | Pre-injection | 70 lbs dumbbell curls | 100 lbs dumbbell curls |
| | 12 Months Post-injection | 100 lbs dumbbell curls | 125 lbs dumbbell curls |
| | 18 Months Post-injection | 115 lbs dumbbell curls | 150 lbs dumbbell curls |
| Triceps | Pre-injection | 100 lbs triceps pressdown | 130 lbs triceps pressdown |
| | 12 Months Post-injection | 120 lbs triceps pressdown | 150 lbs triceps pressdown |
| | 24 Months Post-injection | 140 lbs triceps pressdown | 180 lbs triceps pressdown |
| Chest | Pre-injection | 185 lbs bench press | 225 lbs bench press |
| | 12 Months Post-injection | 245 lbs bench press | 305 lbs bench press |
| Calves | Pre-injection | 120 lbs standing calf raises | 160 lbs standing calf raises |
| | 12 Months Post-injection | 150 lbs standing calf raises | 190 lbs standing calf raises |
| Glutes | Pre-injection | 145 lbs squats | 185 lbs squat |
| | 12 Months Post-injection | 225 lbs squats | 295 lbs squat |
| Shoulders | Pre-injection | 90 lbs military press | 130 lbs military press |
| | 12 Months Post-injection | 135 lbs military press | 185 lbs military press |

Example 10. Gluteus Maximus Augmentation

A healthy 38 year old male weighing approximately 95 kg, with a height of approximately 180 cm was selected to undergo gluteus maximus augmentation. The patient had no pre-existing medical conditions and consented to the procedure. The patient had been previously injected with 1 cc doses of hyaluronic acid at remote locations and showed no clinical evidence of unfavourable reactions at one year post treatment.

The patient was undressed from the waist down to his underwear and had been instructed to wear an undergarment to provide for a completely exposed gluteal surface.

Figure 10A:
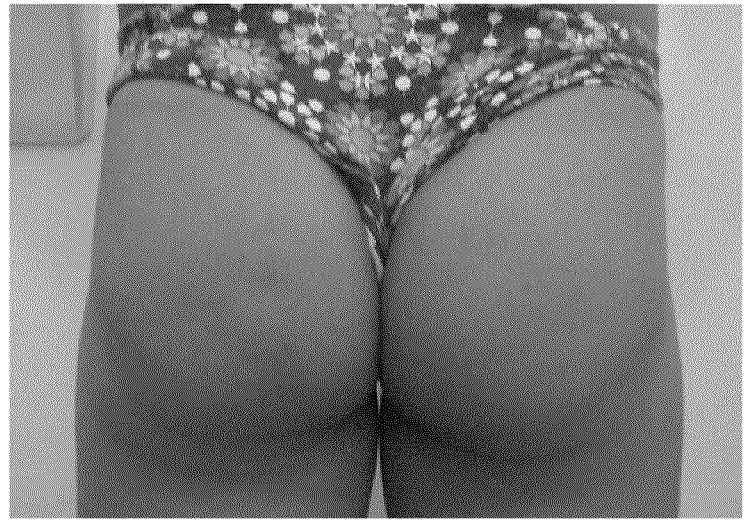
FIG. 10 presents a digital image of a posterior view of the male patient's buttocks of Example 10 to illustrate the gluteus maximus muscle: (A) prior to injection of the composition comprising HA; and (B) at one week post-injection of the composition comprising HA.

Digital photographs were taken against a white backdrop at five level angles: posterior median, mid-scapular (right and left), and mid-axillary (right and left). Photographs were then printed on 4"×6" photo paper and 8.5"×11" plain paper (see FIG. 10A). Photographs were shown to the patient and the desired clinical augmentation lines were sketched on the plain paper in accordance with the patient's wishes. Injection sites were marked on the plain paper with an "X" and subsequently marked on the corresponding sites on the patient with a black surgical marker.

Thirty minutes prior to the procedure, the patient was given medication in the form of oral hydromorphone 6 mg and dimenhydrinate 50 mg in order to palliate any secondary injection pain.

60 cc of cross-linked sodium hyaluronate (Modélis Shape) was prepared for intra-muscular injection, with 2 cc in 30 3 cc syringes. A 25G 1.5" large bore needle was attached to each syringe and set aside for injection. Given the larger injection volume associated with this procedure, xylocaine was not included in the injection mixture as there was concern that xylocaine toxicity may become as issue.

The area to be treated was cleaned thoroughly with sterile gauze soaked in Chlorhexidine 2% with 4% isopropyl alcohol. Intramuscular injection was achieved with a perpendicular approach to the skin at the pre-determined "X" injection sites. 2 cc was injected at each of 30 injection sites. The needle was advanced through the subcutaneous tissue and pierced through the proximal muscular sheath. Injections were subsequently deposited evenly along the injection tract at three locations within the gluteus maximus muscle: about 3.0 cm, about 2.0 cm, and about 1.0 cm from the proximal aspect of the muscular sheath. Negative pressure was applied prior to any injection to assure that the vasculature was not injected. Manual pressure was repetitively applied to injection sites to ensure even distribution of the injectable composition in the local surrounding tissues. Clinical response was observed after each injection. Manual pressure was applied to any bleeding from an injection site and hemostasis was achieved as a contingency for the advancement to the next injection site. The entire process was duplicated for the contralateral side.

The patient had baseline creatine kinase and C-reactive protein measurements done prior to and subsequent to the procedure, which are laboratory makers indicative of muscular damage and inflammation, respectively. The patient was instructed to maintain excellent hydration for one week following the procedure to ensure adequate glomerular filtration rate.

Figure 10B:
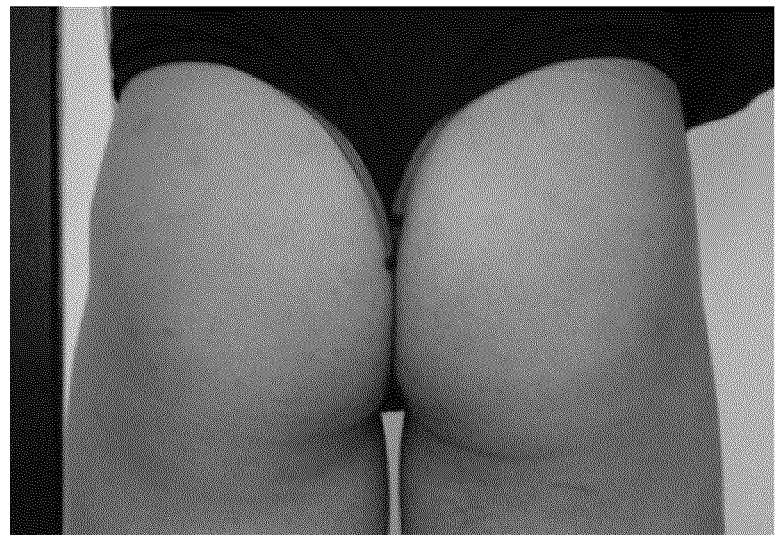

Results:

The patient had a subsequent follow-up at 1 week without any signs of complication. Digital photographs were taken in a manner identical to that described above at 1 week post-injection (see FIG. 10B). Persistent volume augmentation and favourable cosmetic outcome were observed.

All citations are hereby incorporated by reference, as if each individual publication was specifically and individually indicated to be incorporated by reference herein and as though it were fully set forth herein. Citation of references herein is not to be construed nor considered as an admission that such references are prior art to the present invention.

The present invention has been described with regard to one or more embodiments. However, it will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. A method for increasing muscular volume of a muscle in a human comprising, injecting a composition comprising hyaluronic acid (HA) intramuscularly into one or more than one location thereby increasing the muscular volume as compared to the muscular volume prior to the step of injecting, wherein the muscle injected is selected from the group consisting of an arm muscle, a leg muscle, a chest muscle, a back muscle, a buttock muscle, and a latissimus dorsi of the upper back, wherein the composition is a non-sized homogenous gel HA composition or is a particulate HA composition having gel particles with a diameter of 50 µm to 1000 µm.

2. The method of claim 1, wherein increasing the muscular volume improves muscle function of the muscle as compared to the muscle function prior to the step of injecting.

3. The method of claim 1, wherein the composition comprises approximately 0.5 mg/mL to approximately 40 mg/mL of cross-linked HA.

4. The method of claim 3, wherein the composition comprises approximately 10 mg/mL to approximately 30 mg/mL of cross-linked HA.

5. The method of claim 4, wherein the composition comprises approximately 25 mg/mL of cross-linked HA.

6. A method for altering a contour of a muscle in a human comprising, obtaining an image of the contour of the muscle, determining a new contour of the muscle, injecting a composition comprising hyaluronic acid (HA) intramuscularly into one or more than one location of the muscle to obtain the new contour, thereby altering the contour of the muscle as compared to the contour prior to the step of injecting, wherein the composition is a non-sized homogenous gel HA or is a particulate HA composition having gel particles with a diameter of 50 µm to 1000 µm.

7. The method of claim 6, wherein altering the contour of the muscle improves muscle function of the muscle as compared to the muscle function in the absence of the composition.

8. The method of claim 6, wherein the composition comprises approximately 0.5 mg/mL to approximately 40 mg/mL of cross-linked HA.

9. The method of claim 8, wherein the composition comprises approximately 10 mg/mL to approximately 30 mg/mL of cross-linked HA.

10. The method of claim 8, wherein the composition comprises approximately 25 mg/mL of cross-linked HA.

11. The method of claim 1, wherein the composition is the non-sized homogenous gel HA composition.

12. The method of claim 6, wherein the composition is the non-sized homogenous gel HA composition.

13. The method of claim 1, wherein the composition is the particulate HA composition having gel particles with a diameter of 50 µm to 1000 µm.

14. The method of claim 6, wherein the composition is the particulate HA composition having gel particles with a diameter of 50 µm to 1000 µm.

* * * * *